(12) United States Patent
Nickisch et al.

(10) Patent No.: US 7,960,368 B2
(45) Date of Patent: Jun. 14, 2011

(54) BISMETHYLENE-17A CARBOLACTONES AND RELATED USES

(75) Inventors: Klaus Nickisch, Berlin (DE); Pemmaranu N. Rao, San Antonio, TX (US); James W. Cessac, San Antonio, TX (US); Anne Marie Simmons, San Antonio, TX (US)

(73) Assignee: Everstra, Inc., San Antonio, TX (US)

( * ) Notice: Subject to any disclaimer, the term of this patent is extended or adjusted under 35 U.S.C. 154(b) by 0 days.

(21) Appl. No.: 12/397,996

(22) Filed: Mar. 4, 2009

(65) Prior Publication Data
US 2010/0130455 A1  May 27, 2010

Related U.S. Application Data

(60) Provisional application No. 61/033,944, filed on Mar. 5, 2008.

(51) Int. Cl.
*C07D 307/94* (2006.01)
*C07J 53/00* (2006.01)
*A61K 31/56* (2006.01)

(52) U.S. Cl. .......... 514/177; 549/265; 540/15; 514/178; 514/180

(58) Field of Classification Search .......... 514/177, 514/178, 180, 182; 549/265; 540/15
See application file for complete search history.

(56) References Cited

U.S. PATENT DOCUMENTS

| | | | |
|---|---|---|---|
| 3,272,803 A | | 9/1966 | Holden |
| 3,400,136 A | * | 9/1968 | Holden .......... 552/508 |
| 3,463,776 A | * | 8/1969 | Lester et al. .......... 540/11 |
| 3,510,477 A | | 5/1970 | Manson |
| 3,966,713 A | | 6/1976 | Hofmeister et al. |
| 4,129,564 A | | 12/1978 | Wiechert et al. |
| 4,435,327 A | | 3/1984 | Petzoldt |
| 4,501,695 A | | 2/1985 | Van Rheenen et al. |
| 4,584,288 A | | 4/1986 | Nickisch et al. |
| 4,868,166 A | | 9/1989 | Bittler et al. |
| 4,891,365 A | * | 1/1990 | Wiechert et al. .......... 514/173 |
| 5,554,603 A | | 9/1996 | Kim et al. |
| 6,121,465 A | | 9/2000 | Mohr et al. |
| 6,147,066 A | * | 11/2000 | Petit et al. .......... 514/178 |
| 6,887,991 B1 | * | 5/2005 | Ng et al. .......... 540/23 |
| 6,933,395 B1 | | 8/2005 | Mohr et al. |
| 7,319,154 B2 | | 1/2008 | Seilz |
| 2004/0024202 A1 | | 2/2004 | Miller et al. |
| 2005/0192450 A1 | | 9/2005 | Costantino et al. |
| 2006/0264412 A1 | | 11/2006 | Franczyk et al. |
| 2007/0049747 A1 | | 3/2007 | Seilz et al. |
| 2008/0076915 A1 | | 3/2008 | Cabri et al. |
| 2008/0200668 A1 | | 8/2008 | Soros et al. |
| 2008/0207575 A1 | | 8/2008 | Costantino et al. |
| 2009/0023914 A1 | | 1/2009 | Pontiroli et al. |

FOREIGN PATENT DOCUMENTS

DE  3022337  1/1982

OTHER PUBLICATIONS

Soiyom et al., 1985:615646 HCAPLUS, Document No. 103:215646.*
Jiang et al. "New progesterone receptor antagonists: Phosphorus-containing 11b-aryl-substituted steroids" Bioorganic & Medicinal Chemistry 14 (2006) 6726-6732.
Teutsch et al. "Synthesis of a Fluorescent Steroid Derivative With High Affinities for the Glucocorticoid and Progesterone Receptors" Steroids (1994), 59, 22-26.
Nickisch et al. "Säure-Katalysierte Umlagerungen Von 15β,16β-Methylen-17a-Pregnen 21,17-Carbolacton-Derivaten" Tetrahedron Letters, vol. 27, No. 45, 5463-5466.
Giangrande et al. Molecular and Cellular Biology, "The Opposing Transcriptional Activities of the Two Isoforms of the Human Progesterone Receptor Are Due to Differential Cofactor Binding" vol. 20, No. 9, May 2000, p. 3102-3115.
Rao et al. "New 11b-aryl-substituted steroids exhibit both progestational and antiprogestational activity" Steroids 63:523-530, 1998.
Kamata et al. "Aldosterone Antagonists. 2. Synthesis and Biological Activities of 11,12-Dehydropregnane Derivatives" Journal of Medicinal Chemistry, 1987, vol. 30, No. 9, p. 1647-1658.
Nickisch et al. "Aldosterone Antagonists. 1. Synthesis and Activities of 6@,7@:15@,16@-Dimethylene Steroidal Spirolactones" J. Med. Chem. 1985,28, 546-550.
Nickisch et al. "Aldosterone Antagonists. 4. Synthesis and Activities of Steroidal 6,6-Ethylene-15,16-methylene 17-Spirolactones" J. Med. Chem. 1991,34, 2464-2468.
Desai et al. "A Simple High-Yielding Synthesis of Spiro[cyclopropane-1,2'-steroids" Liebigs Ann. Chem., 1990, 711.
Kagawa "Anti-Aldosterones" in Methods in Hormone Research vol. 3 R:I: Dorfmann Academic Press p. 351.
Warwel et al. "Synthese primarer Akylarene ohne Benzol via Olefin-Metathese" Angew. Chem. 94, 1982, 718-719.

* cited by examiner

*Primary Examiner* — Sabiha Qazi
(74) *Attorney, Agent, or Firm* — Meyertons, Hood, Kivlin, Kowert & Goetzel, P.C.; Eric B. Meyertons

(57) ABSTRACT

Described herein are bismethylene-17α carbolactone derivatives having progestational and/or antimineralocorticoid and/or aldosterone antagonistic activity. Also described herein are methods of preparing and using these novel compounds.

25 Claims, 2 Drawing Sheets

BISMETHYLENE-17A CARBOLACTONES AND RELATED USES

PRIORITY CLAIM

This application claims priority to U.S. Provisional Patent Application No. 61/033,944 entitled "Bismethylene-17A Carbolactones and Related Uses" filed on Mar. 5, 2008.

BACKGROUND OF THE INVENTION

1. Field of the Invention

The present invention is generally directed to novel bismethylene-17α carbolactones. More particularly, the invention is related to such derivatives having progestational and aldosterone antagonistic activity and methods of preparing and using these compounds.

2. Description of the Relevant Art

Many of the side effects associated with oral contraceptive pills and hormone replacement therapies are due to administration of hormones. Some of the potential side effects from contraceptives and hormone replacement therapies include: depression, vaginal discharge, changes in menstrual flow, breakthrough bleeding, nausea, vomiting, headaches, changes in the breasts, changes in blood pressure, loss of scalp hair, skin problems and skin improvements, increased risk of deep venous thrombosis (DVT) and pulmonary embolism, stroke, increased incidence of cancer, and myocardial infarction (heart attack). The incidence of various side effects appears to be related, to some extent, on the dosage of the progestogen and, in some cases, the estrogen components.

One of the most commonly used combined progestogens is 6β,7β,15β,16β-dimethylene-3-oxo-17α-pregn-4-ene-21,17-carbolactone (drospirenone). This compound is described in German Patent No. 3,022,337. Drospirenone, however, is only sparingly soluble in water at various pH values. The low aqueous solubility of drospirenone reduces its effectiveness due to poor bioavailability. For example, the absolute bioavailability of drospirenone from a single entity tablet is about 76%.

Other methylene-substituted-17α carbolactones have been reported to exhibit the combination of progestational and antialdosterone antagonistic activity. In EP 0 150 157, 6,6-ethylene-15,16-methylene carbolactones are described that exhibit a strong progestational and antialdosterone activity. EP 0 255 464 reports 2,2:6,6-diethylene-3-oxo-17α-pregn-4-ene 21,17-carbolactones having a stronger anti mineralcorticoid activity with a somewhat reduced progestational activity. As described in EP 0 150 157, these compounds are primarily suited for contraceptive use in women with cardiovascular risk factors such as obesity, age, smoking and elevated blood pressure.

Additionally, under acidic conditions (such as encountered in the gastric environment) 17α carbolactones (e.g., drospirenone) undergo isomerization to a form that is inactive. The combination of poor aqueous solubility and potential for isomerization makes the use of low dosage forms of 17α carbolactones difficult. This leads to the use of higher than necessary amounts of 17α carbolactones to counteract the inactivation and slow absorption of the active form.

The use of high dosages of a 17α carbolactones progestogen may lead to an increase in the occurrence of side effects. It is therefore desirable to develop 17α carbolactones progestogens that are highly effective for use in contraceptive and hormone replacement therapies, that are more resistant to the gastric environment, exhibit improved bioavailability, and/or reduce the incidence of side effects.

SUMMARY OF THE INVENTION

In one embodiment, an antimineralocorticoid compound has the structure of formula (I):

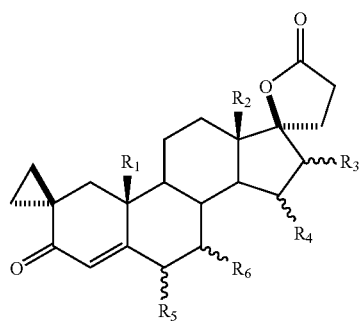

where:
- $R_1$ is H or $CH_3$;
- $R_2$ is $CH_3$ or $CH_2CH_3$;
- $R_3$ and $R_4$ are hydrogens; together form an α-$CH_2$ bridge between carbons 15 and 16; or together form a β-$CH_2$ bridge between carbons 15 and 16; and
- $R_5$ and $R_6$ together form an α-$CH_2$ bridge between carbons 6 and 7 or a β-$CH_2$ bridge between carbons 6 and 7.

Compounds of formula (I) may be used as an aldosterone antagonist, a diuretic, or an anti hypertensive when an oral dosage form comprising an effective amount of an antimineralocorticoid compound (I) is administered to the subject.

In another embodiment, a progestogen compound has the structure of formula (II):

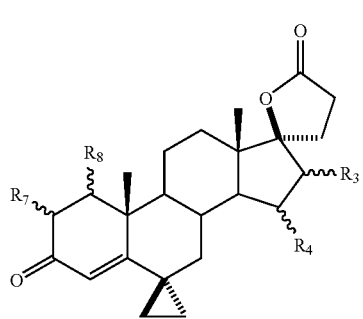

where:
- $R_3$ and $R_4$ together form an α-$CH_2$ bridge between carbons 15 and 16 or a β-$CH_2$ bridge between carbons 15 and 16; and
- $R_7$ and $R_8$ are hydrogens; together form an additional bond between carbons 1 and 2; together form an α-$CH_2$ bridge between carbons 1 and 2; or together form a β-$CH_2$ bridge between carbons 1 and 2.

Compounds of formula (II) may be used to produce a contraceptive state in a subject when an oral dosage form comprising an effective amount of a progestogen compound (II) is administered to the subject.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
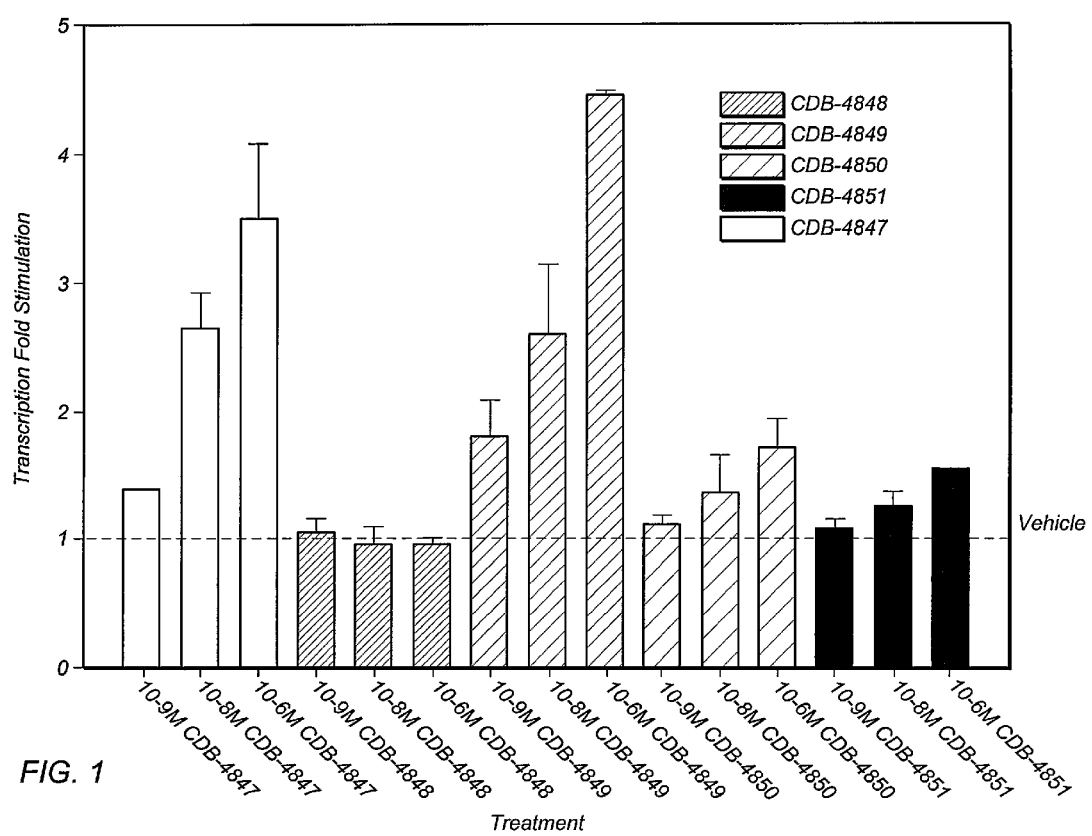
FIG. 1 depicts results from the transient transfection of CV-1 Cells with 3XHRE-tk-LUC and a human mineralocorticoid expression vector (pchMR)

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

Described herein are progestogen and antimineralocorticoid compounds, methods of making these compounds and methods of using these compounds. Progestogens are hormones that produce effects similar to those of progesterone. Progestogens have antiestrogenic (counteracting the effects of estrogens on the body) and antigonadotropic (inhibiting the production of sex steroids by gonads) properties. For the structures described herein, the standard steroid numbering scheme is used. Specifically, steroids are numbered according to the general formula below.

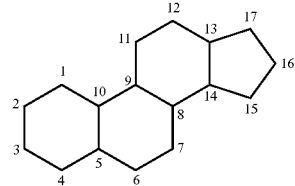

In one embodiment, an antimineralocorticoid compound has the structure of formula (I):

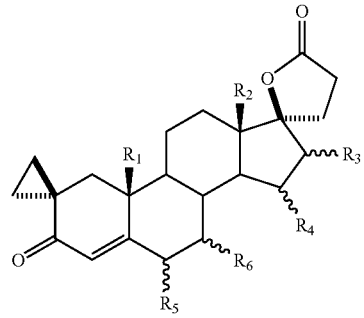

where:

$R_1$ is H or $CH_3$;

$R_2$ is $CH_3$ or $CH_2CH_3$;

$R_3$ and $R_4$ are hydrogens; or together form an $\alpha$-$CH_2$ bridge between carbons 15 and 16; or a $\beta$-$CH_2$ bridge between carbons 15 and 16; and $R_5$ and $R_6$ together form an $\alpha$-$CH_2$ bridge between carbons 6 and 7 or a $\beta$-$CH_2$ bridge between carbons 6 and 7.

When $R_1$ is $CH_3$ and $R_2$ is $CH_3$, the an antimineralocorticoid compound has the structure of formula (III):

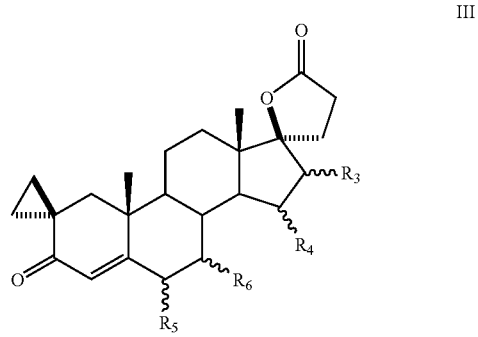

where $R_3$ and $R_4$ are hydrogens; or together form an $\alpha$-$CH_2$ bridge between carbons 15 and 16; or a $\beta$-$CH_2$ bridge between carbons 15 and 16; and $R_5$ and $R_6$ together form an $\alpha$-$CH_2$ bridge between carbons 6 and 7 or a $\beta$-$CH_2$ bridge between carbons 6 and 7.

Specific examples include:

IIIa:

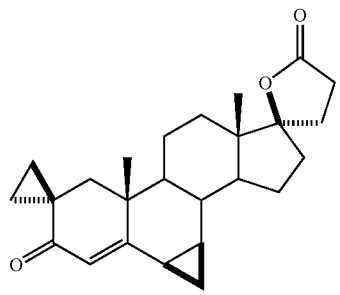

$R_3, R_4 = H$
$R_5, R_6 = \beta$-$CH_2$ bridge

IIIb:

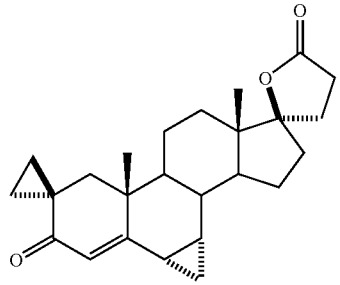

$R_3, R_4 = H$
$R_5, R_6 = \alpha$-$CH_2$ bridge

-continued

IIIc:

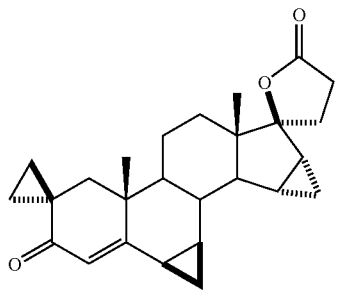

R₃, R₄ = α-CH₂ bridge
R₅, R₆ = β-CH₂ bridge

IIId:

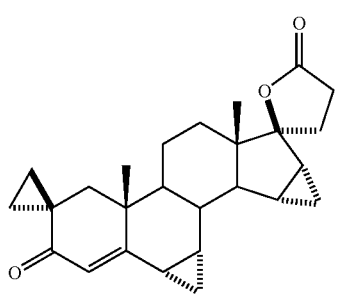

R₃, R₄ = α-CH₂ bridge
R₅, R₆ = α-CH₂ bridge

IIIe:

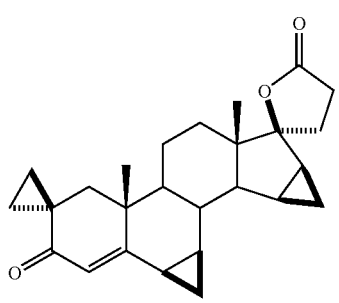

R₃, R₄ = β-CH₂ bridge
R₅, R₆ = β-CH₂ bridge

IIIf:

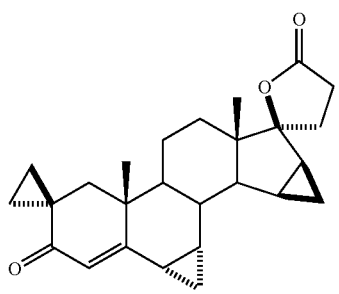

R₃, R₄ = β-CH₂ bridge
R₅, R₆ = α-CH₂ bridge

In another embodiment, a progestogen compound has the structure of formula (II):

II

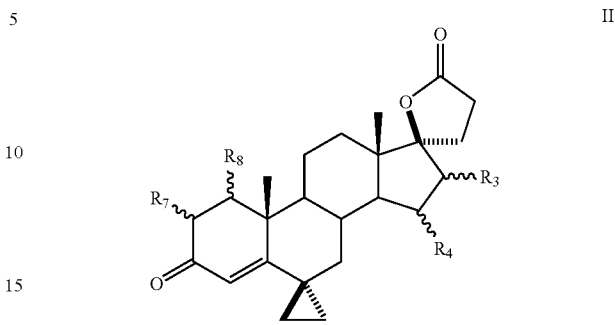

Where:

$R_3$ and $R_4$ together form an α-CH₂ bridge between carbons 15 and 16 or a β-CH₂ bridge between carbons 15 and 16; and $R_7$ and $R_8$ are hydrogens; together form an additional bond between carbons 1 and 2; or together form an α-CH₂ bridge between carbons 1 and 2.

When $R_3$ and $R_4$ are a β-CH₂ bridge between carbons 15 and 16, the progestogen compound has the structure of formula (IV):

IV

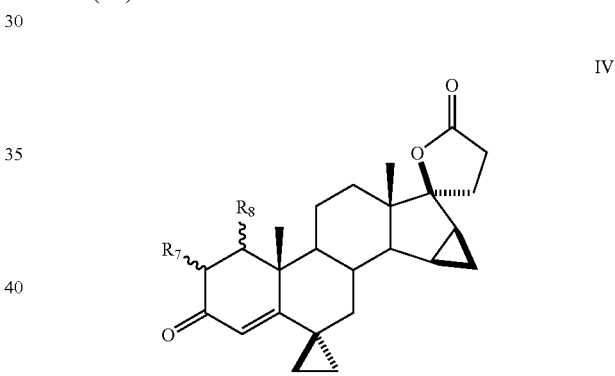

where $R_7$ and $R_8$ are hydrogens; together form an additional bond between carbons 1 and 2; or together form an α-CH₂ bridge between carbons 1 and 2.

Specific examples include:

IVa:

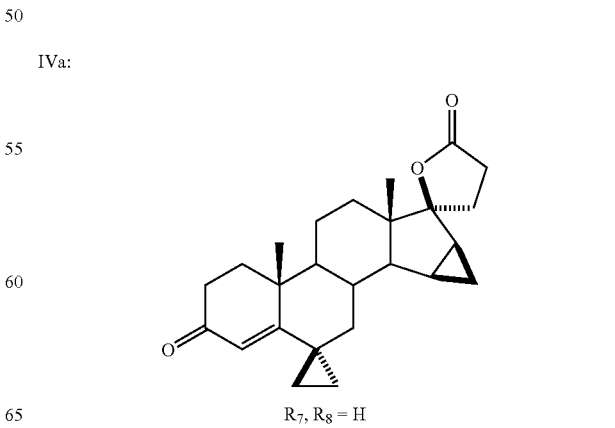

R₇, R₈ = H

IVb:

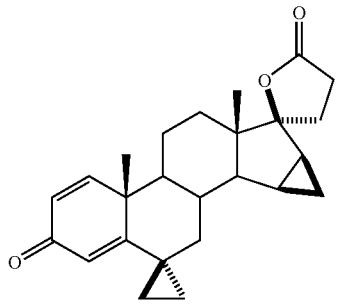

R$_7$, R$_8$ = additional bond

IVc:

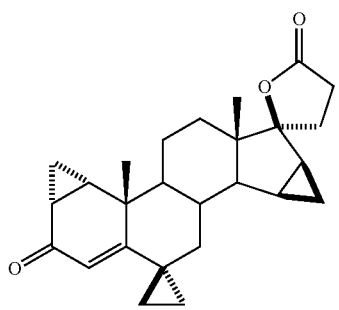

R$_7$, R$_8$ = α-CH$_2$ bridge

The above described progestogen compounds show a more balanced endocrinological profile, exhibiting strong progestational and antimineralocorticoid activity making them ideal candidates for use as contraceptives.

The compounds of general structure (I) maybe prepared from the corresponding compounds of general structure (V), as shown below in Scheme 1, where R$_1$, R$_2$, R$_3$, R$_4$, R$_5$, and R$_6$ are as defined above. Reaction of compounds of general formula (V) with a methylene ylid gives the target compounds of general formula (I). In one embodiment, the conversion of compounds of general structure (V) may be converted to compounds of general structure (I) using Simmons Smith reaction (i.e., a Zn\Cu stabilized methylide) as described in Desai, U. R., Trivedi, G. K., Liebigs Ann. Chem., 1990, 711, which is incorporated herein by reference. Phosphorous or sulfur ylids may also be used. In one embodiment, the reagent dimethylsulfoxonium methylide formed by the reaction of trimethylsulfoxonium iodide and a strong base (e.g., NaH) in an aprotic solvent (e.g., dimethylsulfoxide) may be used. Examples of this process may be found, for example, in U.S. Pat. No. 3,272,803, which is incorporated herein by reference. In another example, diazomethane may be used as a methylide equivalent. The diazomethane may be reacted with compounds having the general structure (V) and the resulting intermediate pyrazoline decomposed with acid to give compounds having the general structure (I). Examples of this process may be found, for example, in U.S. Pat. No. 3,510,477, which is incorporated herein by reference.

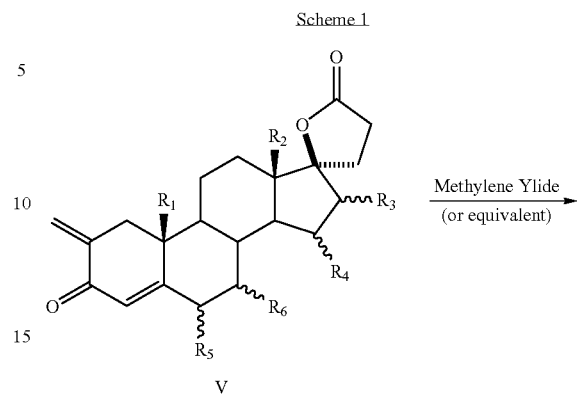

Scheme 1

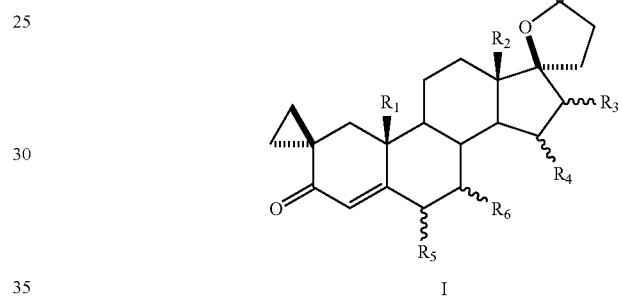

The compounds of general structure (I) may also be prepared from the corresponding compounds of general structure (VI), as shown below in Scheme 2, where R$_1$, R$_2$, R$_3$, R$_4$, R$_5$, and R$_6$ are as defined above. Reaction of compounds of general structure (VI) with a base in the presence of formaldehyde or a formaldehyde equivalent (for example, formalin, halomethyl alkyl ethers, dialkoxymethanes (such as dimethoxymethane or diethoxymethane), etc.) yields the desired 6-hydroxymethyl compounds of general formula (VII). In one embodiment, treatment of compound (VI) with pyrrolidine generates the 3-enamine, which is reacted with formalin to give the 2-hydroxymethyl derivative (VII).

Scheme 2

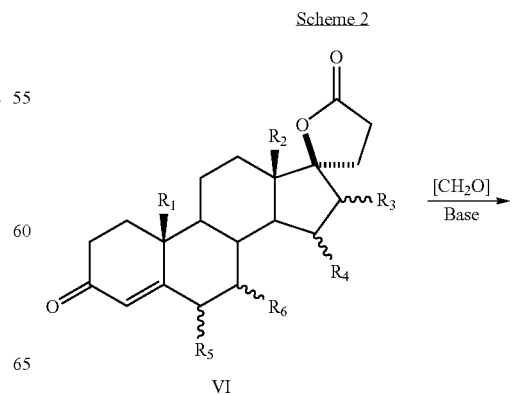

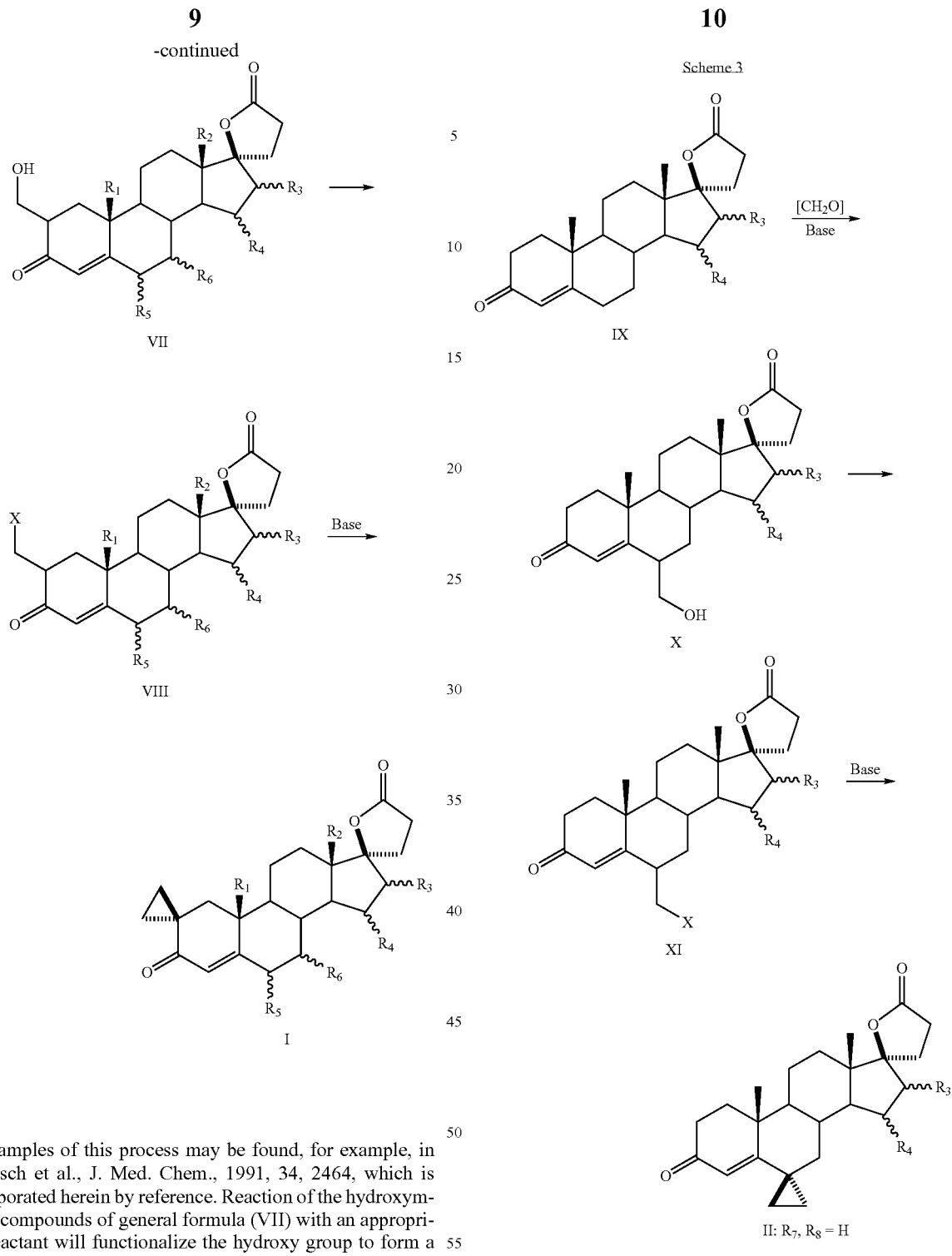

Examples of this process may be found, for example, in Nickisch et al., J. Med. Chem., 1991, 34, 2464, which is incorporated herein by reference. Reaction of the hydroxymethyl compounds of general formula (VII) with an appropriate reactant will functionalize the hydroxy group to form a leaving group "X" as depicted in formula (VIII). Examples of leaving groups include, but are not limited to I, Cl, Br, tosyl, brosyl, mesyl, or trifyl. Finally, treatment of the compounds of general formula (VIII) with a methylene ylid gives the target compounds of general formula (II, $R_1$, $R_2$=H). Phosphorous or sulfur ylids may be used. In one embodiment, a sulfur ylid formed by the reaction of trimethylsulfoxonium iodide and a strong base (e.g., NaH) in an aprotic solvent (e.g., dimethylsulfoxide) may be used.

Compounds of general formula (II) wherein $R_7$ and $R_8$ represent hydrogen may be synthesized according to the sequence shown below in Scheme 3.

Reaction of compounds of general structure (IX) with a base in the presence of formaldehyde or a formaldehyde equivalent (for example, formalin, halomethyl alkyl ethers, dialkoxymethanes (such as dimethoxymethane or diethoxymethane), etc.) yields the desired 6-hydroxymethyl compounds of general formula (X). Reaction of the hydroxymethyl compounds of general formula (X) with an appropriate reactant will functionalize the hydroxy group to form a leaving group "X" as depicted in formula (XI). Examples of leaving groups include, but are not limited to I, Cl, Br, tosyl, brosyl, mesyl, or trifyl. Finally, treatment of the compounds of general formula (XI) with a methylene ylid gives the target compounds of general formula (II, $R_7$, $R_8$=H). Phosphorous or sulfur ylids may be used. In one embodiment, a sulfur ylid formed by the reaction of trimethylsulfoxonium iodide and a strong base (e.g., NaH) in an aprotic solvent (e.g., dimethylsulfoxide)) may be used. Examples of this general process may be found, for example, in U.S. Pat. No. 7,319,154, which is incorporated herein by reference.

Reaction of compounds of general structure (II, $R_7$, $R_8$ are hydrogen) with a suitable dehydrogenating agent gives the corresponding diene derivatives of general formula (II, $R_7$, $R_8$ form a double bond) as shown in Scheme 4. Examples of suitable dehydrogenating agents include, but are not limited to, metals (e.g., Pd, Pt, etc.), sulfur, selenium, and quinones (e.g., dichlorodicyanoquinone, tetrachloroquinone, etc.).

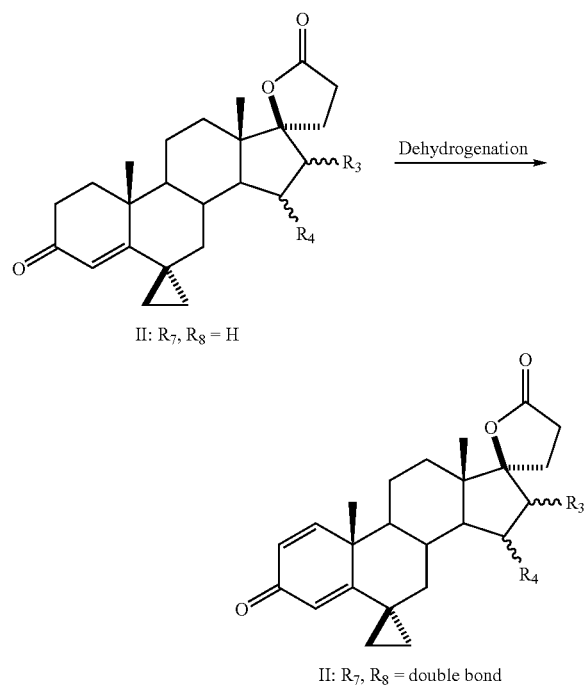

Compounds of general formula (I) wherein $R_1$ and $R_2$ represent a $CH_2$ bridging group may be prepared as indicated below in Scheme 5. Examples of this procedure may be found, for example, in J. Med Chem. 1985, 28, 546-550, which is incorporated herein by reference. Reaction of compounds of general formula (II: $R_7$, $R_8$=double bond) with a methylene ylid gives the target compounds of general formula (II: $R_7$, $R_8$=$CH_2$). In one embodiment, the conversion of compounds of general structure (II: $R_2$, $R_8$=double bond) may be converted to compounds of general structure (II: $R_7$, $R_8$=$CH_2$) using Simmons Smith reaction (i.e., a Zn\Cu stabilized methylide) as described in Desai, U. R., Trivedi, G. K., Liebigs Ann. Chem., 1990, 711, which is incorporated herein by reference. Phosphorous or sulfur ylids may also be used. In one embodiment, the reagent dimethylsulfoxonium methylide formed by the reaction of trimethylsulfoxonium iodide and a strong base (e.g., NaH) in an aprotic solvent (e.g., dimethylsulfoxide) may be used. Examples of this process may be found, for example, in U.S. Pat. No. 3,272,803, which is incorporated herein by reference. In another example, diazomethane may be used as a methylide equivalent. The diazomethane may be reacted with compounds having the general structure (II: $R_7$, $R_8$=double bond) and the resulting intermediate pyrazoline decomposed with acid to give compounds having the general structure (II: $R_7$, $R_8$=$CH_2$). Examples of this process may be found, for example, in U.S. Pat. No. 3,510,477, which is incorporated herein by reference.

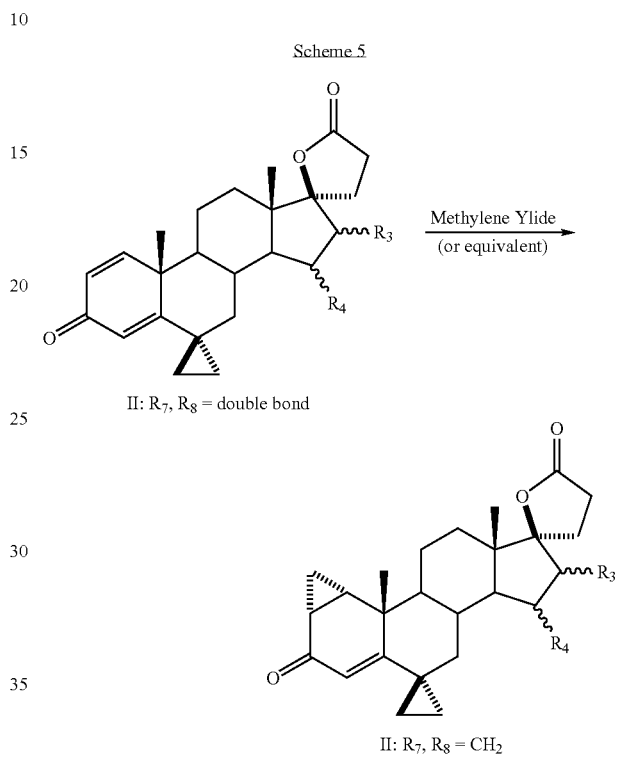

The progestogen compounds described herein may be administered in combination with an estrogen to produce a contraceptive state in a subject. Estrogens include, but are not limited to, estradiol (17β-estradiol), estridiol acetate, estradiol benzoate, estridiol cypionate, estridiol decanoate, estradiol diacetate, estradiol heptanoate, estradiol valerate, 17α-estradiol, estriol, estriol succinate, estrone, estrone acetate, estrone sulfate, estropipate (piperazine estrone sulfate), ethynylestradiol (17α-ethynylestradiol, ethinylestradiol, ethinyl estradiol, ethynyl estradiol), ethynylestradiol 3-acetate, ethynylestradiol 3-benzoate, mestranol, quinestrol, and nitrated estrogen derivatives. Nitrated estrogen derivatives are described in U.S. Pat. No. 5,554,603 to Kim et al., which is incorporated herein by reference. In some embodiments, the progestogen compounds described herein may be combined with ethinylestradiol to produce a contraceptive state in a subject.

The progestogen compounds and antimineralocorticoid compounds described herein may be administered to a subject by combining the compounds with one or more pharmaceutically acceptable carriers selected to provide the progestogen compound to the subject. As used herein the phrase pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Any suitable route of administration may be employed for providing a subject with an effective dosage of progestogen compounds. For example, oral, transmucosal, parenteral, subcutaneous, intravenous, intracoronary, intramuscular, intra-peritoneal, pulmonary, nasal, transdermal, ocular, or rectal, routes and the like may be employed. Dosage forms include tablets, troches, dispersions, suspensions, solutions, capsules, creams, ointments, aerosols, and the like. In certain embodiments, it may be advantageous that the compositions described herein be administered orally.

In some embodiments the oral dosage form is monolithic and substantially solid, that is, it is formed as a unitary mass that is molded, freeze dried, cut, ground or otherwise formed in its final shape. In other embodiments, the oral dosage form may be an aggregate or composite of individual solid particulates, pellets, beads, granules, sprinkles, triturates, microspheres or the like formed into a tablet or disposed in a capsule. The phrase "oral dosage form" as used herein refers to pharmaceutical compositions formed as tablets, caplets, softlets, films, troche, sachet, wafers and the like. In some embodiments, the oral dosage forms are capable of disintegrating or dissolving when contacted with saliva of the buccal and/or sublingual cavity.

Oral dosage forms described herein for use as an oral contraceptive include at least a progestogen in an amount effective to inhibit ovulation in a female subject. An oral dosage form may include, but is not limited to, between about 0.5 mg to about 50 mg, between about 1 mg to 30 mg, or between about 2 mg to 10 mg of a progestogen. An oral dosage form includes, but is not limited to, 1 mg, 1.5 mg, 2 mg, 2.5 mg, 3 mg, 3.5 mg, 4 mg, 4.5 mg, or 5 mg of a progestogen.

In addition to a progestogen, an oral dosage form may further include an estrogen. An oral dosage form may include, but is not limited to, between about 0.01 mg to about 0.1 mg, between about 0.015 mg to 0.075 mg, or between about 0.02 mg to 0.05 mg of an estrogen. An oral dosage form includes, but is not limited to, 0.01 mg, 0.015 mg, 0.02 mg, 0.025 mg, 0.03 mg, 0.035 mg, 0.04 mg, 0.045 mg, 0.05 mg, or 0.06 mg of an estrogen.

The progestogen compound may be incorporated into a tablet for use as an oral dosage form. The progestogen compound may be made into progestogen particles using any type of granulation process, such as the processes described below, or other mixing techniques known in the art. In one embodiment, the progestogen compound may be in a micronized form. In an embodiment, an inactive ingredient, usually referred to as a binder, is mixed with the progestogen particles to help hold the tablet together and give it strength. A wide variety of binders may be used and are well known in the art. After mixing is complete, the tablet formulation may be placed in a tablet press and compressed to form a tablet.

In other embodiments, an oral dosage form includes an enteric polymer in which a progestogen compound or an antimineralocorticoid compound is dispersed. In an embodiment, the enteric polymer is a fusible, thermoplastic or thermosetting material, typically a resin or polymer. An enteric polymer may make up about 20% to about 99.9% of the oral dosage form by weight, or at least about 30%, at least about 40%, or at least about 50% of the oral dosage form by weight.

As used herein the term "enteric polymer" is a polymer that is substantially insoluble and/or impermeable to the acidic environment of the stomach (e.g., pH of about 1-3) and soluble or permeable in the environment of the intestine (pH of about 5-7). An enteric polymer, as defined herein, releases less than 10% of a therapeutic agent dispersed in the enteric polymer after 2 hours of stirring the dispersion in a 0.1 N HCl solution and releases more than about 10% of a therapeutic agent dispersed in the enteric polymer after about 2 hours stirring in a pH 6.8 phosphate buffer solution.

As used herein the term "dispersed", with respect to a polymer matrix, means that a compound is substantially evenly distributed through the polymer, either as a solid suspension in the polymer or dissolved within the polymer matrix.

The release characteristics of the oral dosage form can be determined in vitro using simulated gastric or intestinal fluids, but is preferably determined in vivo by monitoring blood levels of the therapeutic agent in subjects that have ingested the oral dosage form. Methods of determining the in vivo and in vitro release of therapeutic agents from oral dosage forms are well-known to those skilled in the art.

Enteric polymers may include polymers with acidic functional groups. Enteric polymers may solubilize or become permeable in an aqueous solution at a pH of greater than 5. Examples of enteric polymers include cellulose based enteric polymers, vinyl based enteric polymers, and acrylic acid—methacrylic acid based enteric polymers. As used herein, the phrase "acrylic acid-based polymers" refers to any polymer that includes one or more repeating units that include and/or are derived from acrylic acid. As used herein, the phrase "methacrylic acid-based polymers" refers to any polymer that includes one or more repeating units that include and/or are derived from methacrylic acid.

Examples of cellulose based enteric polymers include, but are not limited to, cellulose acetate phthalate (CAP), cellulose acetate succinate, methylcellulose phthalate, ethylhydroxycellulose phthalate, hydroxypropyl methylcellulose phthalate (HPMCP), hydroxypropyl methylcellulose acetate succinate (HPMCAS), cellulose acetate butyrate, and cellulose acetate trimaleate.

Examples of vinyl based enteric polymers include, but are not limited to, polyvinyl acetate phthalate (PVAP), polyvinylbutyrate acetate, polyvinyl acetate, vinyl acetate-maleic anhydride copolymer, and polyvinyl acetal diethylaminoacetate.

Examples of acrylic acid—methacrylic acid based enteric polymers include, but are not limited to, Eudragit® L30-D55, Eudragit® FS 30D, Eudragit® L 12.5, Eudragit® L 12.5P, Eudragit® L100, Eudragit® L100-55, Eudragit® L-30, Eudragit® LD-55, Eudragit® S 12.5, Eudragit® S 12.5P, Eudragit® S100, Eudragit® S 100-55, Eudragit® NE 30D, Eudragit® RL 12.5, Eudragit® RL 100, Eudragit® RL PO, Eudragit® RL 30D, Eudragit® RS 12.5, Eudragit® RS 100, Eudragit® RS PO, and Eudragit® RS 30D.

One or more water-insoluble polymers may be combined with one or more enteric polymers to form an oral dosage form. Examples of pharmaceutically-acceptable, water-insoluble polymers include, but are not limited to acrylic acid-based polymers, methacrylic acid based polymers, and acrylic acid—methacrylic acid based copolymers. As used herein, the phrase "acrylic acid-based polymers" refers to any polymer that includes one or more repeating units that include and/or are derived from acrylic acid. As used herein, the phrase "methacrylic acid-based polymers" refers to any polymer that includes one or more repeating units that include and/or are derived from methacrylic acid. Derivatives of acrylic acid and methacrylic acid include, but are not limited to, alkyl ester derivatives, alkylether ester derivatives, amide derivatives, alkyl amine derivatives, anhydride derivatives, cyanoalkyl derivatives, and amino-acid derivatives. Examples of acrylic acid-based polymers, methacrylic acid based polymers, and acrylic acid—methacrylic acid based copolymers include, but are nor limited to Eudragit® L100, Eudragit® L100-55, Eudragit® L 30 D-55, Eudragit® 5100, Eudragit® 4135F, Eudragit® RS, acrylic acid and methacrylic acid copolymers, methyl methacrylate polymers, methyl methacrylate copolymers, polyethoxyethyl methacrylate, polycyanoethyl methacrylate, aminoalkyl methacrylate copolymer, polyacrylic acid, polymethacrylic acid, methacrylic acid alkylamine copolymer, polymethyl methacrylate, polymethacrylic acid anhydride, polyalkylmethacrylate, polyacrylamide, and polymethacrylic acid anhydride and glycidyl methacrylate copolymers.

Further examples of pharmaceutically-acceptable, water-insoluble polymers include, but are not limited to, alkylcelluloses such as ethylcellulose, methylcellulose, and calcium carboxymethyl cellulose, and polyesters, waxes, shellac, zein, or the like.

In further embodiments, in addition to containing 20 to 99.9% by weight of one or more enteric polymers, the oral dosage forms may further include one or more pharmaceutically-acceptable hydrophilic matrix materials including water-soluble polymers such as polyethylene oxide (PEO), ethylene oxide-propylene oxide co-polymers, polyethylene-polypropylene glycol (e.g. poloxamer), carbomer, polycarbophil, chitosan, polyvinyl pyrrolidone (PVP), polyvinyl alcohol (PVA), hydroxyalkyl celluloses such as hydroxypropyl cellulose (HPC), hydroxyethyl cellulose, hydroxymethyl cellulose and hydroxypropyl methylcellulose, carboxymethyl cellulose, sodium carboxymethyl cellulose, methylcellulose, hydroxyethyl methylcellulose, hydroxypropyl methylcellulose, polyacrylates such as carbomer, polyacrylamides, polymethacrylamides, polyphosphazines, polyoxazolidines, polyhydroxyalkylcarboxylic acids, alginic acid and its derivatives such as carrageenate alginates, ammonium alginate and sodium alginate, starch and starch derivatives, polysaccharides, carboxypolymethylene, polyethylene glycol, natural gums such as gum guar, gum acacia, gum tragacanth, karaya gum and gum xanthan, povidone, gelatin or the like.

For purposes of the present disclosure, a matrix material is considered hydrophilic and a polymer is considered to be water-soluble if it is more than sparingly soluble as defined by USP 29/NF 24, that is if according to USP 29/NF 24 the matrix material or polymer is classified as "soluble" or "very soluble."

Preferred materials used to produce an oral dosage form will be pharmaceutically acceptable materials, such as those indicated to be generally regarded as safe ("GRAS-certified") or national formulary certified. Pharmaceutically acceptable materials include polymers (e.g., enteric polymers, hydrophilic polymers, and hydrophobic polymers), plasticizers, lubricants, thermal lubricants, antioxidants, buffering agents, alkalinizing agents, disintegrants, binders, diluents, sweeteners, chelating agents, colorants, flavorants, surfactants, solubilizers, wetting agents, stabilizers, hydrophilic polymers, hydrophobic polymers, waxes, lipophilic materials, absorption enhancers, preservatives, absorbents, cross-linking agents, bioadhesive polymers, retardants, pore formers, osmotic agents and fragrance.

In preferred embodiments, a plasticizer is also combined with the enteric polymer to modify the properties of the polymer. Plasticizers interact with the enteric polymer resulting in a lower viscosity of the mixture during extrusion or molding. The result is that extrusion or injection molding of the oral dosage form can occur at lower temperatures, thereby reducing the possibility of thermally degrading the therapeutic agent (e.g., drospirenone or ethinylestradiol). The most suitable plasticizers are those that lower the glass transition temperature (Tg) of the enteric polymer. Plasticizers suitable for use with the compositions and methods disclosed herein include, but are not limited to, low molecular weight polymers, oligomers, copolymers, oils, small organic molecules, low molecular weight polyols having aliphatic hydroxyls, ester-type plasticizers, glycol ethers, polypropylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, acetyl triethyl citrate, tributyl citrate and allyl glycolate.

In addition to an enteric polymer and a therapeutic agent, compositions may also include one or more functional excipients such as lubricants, thermal lubricants, antioxidants, buffering agents, alkalinizing agents, disintegrants, binders, diluents, sweeteners, chelating agents, colorants, flavorants, surfactants, solubilizers, wetting agents, stabilizers, hydrophilic polymers, hydrophobic polymers, waxes, lipophilic materials, absorption enhancers, preservatives, absorbents, cross-linking agents, bioadhesive polymers, retardants, pore formers, osmotic agents and fragrance.

Lubricants or thermal lubricants useful as an excipient include, but are not limited to fatty esters, glyceryl monooleate, glyceryl monostearate, wax, carnauba wax, beeswax, vitamin E succinate, and a combination thereof.

As used herein, the term "antioxidant" is intended to mean an agent that inhibits oxidation and thus is used to prevent the deterioration of preparations by oxidation due to the presence of oxygen free radicals or free metals in the composition. Such compounds include, by way of example and without limitation, ascorbic acid (Vitamin C), ascorbyl palmitate, butylated hydroxyanisole (BHA), butylated hydroxytoluene (BHT), hypophophorous acid, monothioglycerol, sodium ascorbate, sodium formaldehyde sulfoxylate, sodium metabisulfite, sodium bisulfite, vitamin E and its derivatives, propyl gallate and others known to those of ordinary skill in the art.

Binders are ingredients added to mixtures to provide adhesive qualities during and after formation of an oral dosage. Examples of binders include, but are not limited to: waxes such as beeswax; carnauba wax; microcrystalline wax and paraffin wax; cetyl palmitate; glycerol behenate; glyceryl palmitostearate; glyceryl stearate; hydrogenated castor oil; stearic acid; stearic alcohol; stearate 6000 WL1644; gelucire 50/13; polyethylene glycols (PEG) such as PEG 2000, PEG 3000, PEG 6000, PEG 8000, PEG 10000, PEG 20000; polyethylene oxide; polypropylene oxide; polyvinylpyrrolidone; polyvinylpyrrolidone-co-vinylacetate; acrylate-methacrylate copolymers; polyethylene; polycaprolactone; alkylcelluloses such as methylcellulose; hydroxyalkylcelluloses such as hydroxymethylcellulose, hydroxyethyl cellulose, hydroxypropylcellulose, and hydroxybutylcellulose; hydroxyalkyl alkylcelluloses such as hydroxyethyl methylcellulose and hydroxypropyl methylcellulose; starches, pectins; polylactic acid (PLA); polyglycolic acid (PLGA), polyesters (e.g., shellac); and polysaccharides such as cellulose, tragacanth, gum arabic, guar gum, and xanthan gum.

A buffering agent is used to resist change in pH upon dilution or addition of acid or alkali. Such compounds include, by way of example and without limitation, potassium metaphosphate, potassium phosphate, monobasic sodium acetate and sodium citrate anhydrous and dihydrate, salts of inorganic or organic acids, salts of inorganic or organic bases, and others known to those of ordinary skill in the art.

As used herein, the term "alkalizing agent" is intended to mean a compound used to provide alkaline medium for product stability. Such compounds include, by way of example and without limitation, ammonium carbonate, diethanolamine, monoethanolamine, potassium hydroxide, sodium borate, sodium carbonate, sodium bicarbonate, sodium hydroxide, triethanolamine and others known to those of ordinary skill in the art.

As used herein, the term "disintegrant" is intended to mean a compound used in solid dosage forms to promote the disruption of a solid mass (layer) into smaller particles that are more readily dispersed or dissolved. Exemplary disintegrants include, by way of example and without limitation, starches such as corn starch, potato starch, pre-gelatinized and modified starches thereof, sweeteners, clays, bentonite, microcrystalline cellulose (e.g., Avicel™), carboxymethylcellulose calcium, croscarmellose sodium, alginic acid, sodium alginate, cellulose polyacrilin potassium (e.g., Amberlite™), alginates, sodium starch glycolate, gums, agar, guar, locust bean, karaya, pectin, tragacanth, crospovidone and other materials known to one of ordinary skill in the art. A superdisintegrant is a rapidly acting disintegrant. Exemplary superdisintegrants include crospovidone and low substituted HPC.

Exemplary chelating agents include EDTA, polyamines, derivatives thereof, and others known to those of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other FD&C dyes and natural coloring agents such as grape skin extract, beet red powder, beta carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors that have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particular flavors are the grape and cherry flavors and citrus flavors such as orange.

Surfactants include soaps, synthetic detergents, and wetting agents. Suitable surfactants include cationic surfactants, anionic surfactants, non-ionic surfactants, and amphoteric surfactants. Examples of surfactants include Polysorbate 80; sorbitan monooleate; sodium lauryl sulfate (sodium dodecylsulfate); soaps such as fatty acid alkali metal salts, ammonium salts, and triethanolamine salts; cationic detergents such as dimethyl dialkyl ammonium halides, alkyl pyridinium halides, and alkylamine acetates; anionic detergents such as alkyl, aryl and olefin sulfonates, alkyl, olefin, ether and monoglyceride sulfates, and sulfosuccinates; nonionic detergents such as fatty amine oxides, fatty acid alkanolamides, and poly(oxyethylene)-block-poly(oxypropylene)copolymers; and amphoteric detergents, for example, alkyl β-aminopropionates and 2-alkylimidazoline quaternary ammonium salts; wetting agents such as, glycerin, proteins, and peptides; water miscible solvents such as glycols; and mixtures thereof.

Solubilizers include cyclodextrins, povidone, combinations thereof, and others known to those of ordinary skill in the art.

Exemplary hydrophilic polymers which can be a primary or secondary polymeric carrier that can be included in the composition include poly(vinyl alcohol) (PVA), polyethylene-polypropylene glycol (e.g. poloxamer), carbomer, polycarbophil, or chitosan. Hydrophilic polymers include, but are not limited to, one or more of, carboxymethylcellulose, hydroxyalkyl celluloses such as hydroxypropyl cellulose, hydroxyethyl cellulose, hydroxyethyl methyl cellulose, and hydroxymethyl cellulose, methylcellulose, natural gums such as gum guar, gum acacia, gum tragacanth, or gum xanthan and povidone. "Hydrophilic polymers" also include polyethylene oxide, sodium carboxymethycellulose, carboxypolymethylene, polyethylene glycol, alginic acid, gelatin, polyvinyl alcohol, polyvinylpyrrolidones, polyacrylamides, polymethacrylamides, polyphosphazines, polyoxazolidines, poly(hydroxyalkylcarboxylic acids), carrageenate alginates, carbomer, ammonium alginate, sodium alginate, or mixtures thereof.

Exemplary hydrophobic polymers include alkylcelluloses, ethyl cellulose, Eudragit RS, waxes, polyesters, combinations thereof, and others known to those of ordinary skill in the art.

Exemplary waxes include carnauba wax, beeswax, microcrystalline wax and others known to one of ordinary skill in the art.

Exemplary absorption enhancers include dimethyl sulfoxide, Vitamin E PGS, sodium cholate and others known to one of ordinary skill in the art.

Preservatives include compounds used to prevent the growth of microorganisms. Suitable preservatives include, by way of example and without limitation, benzalkonium chloride, benzethonium chloride, benzyl alcohol, cetylpyridinium chloride, chlorobutanol, phenol, phenylethyl alcohol, phenylmercuric nitrate and thimerosal and others known to those of ordinary skill in the art.

Examples of absorbents include sodium starch glycolate (Explotab™, Primojel™); croscarmellose sodium (Ac-Di-Sol®); polyvinylpyrrolidone (PVP) (e.g., Polyplasdone™ XL 10); veegum; clays; alginates; alginic acid; carboxymethylcellulose calcium; microcrystalline cellulose (e.g., Avicel™); polacrillin potassium (e.g., Amberlite™); sodium alginate; corn starch; potato starch; pregelatinized starch; modified starch; cellulosic agents; montmorrilonite clays (e.g., bentonite); gums; agar: locust bean gum; gum karaya; pecitin; tragacanth; and other absorbents known in to those of ordinary skill in the art.

In an embodiment, the oral dosage form may include one or more polycarboxylic acids. Polycarboxylic acids include organic compounds that have two or more carboxyl (—COOH) groups and from 2 to 9 carbon atoms in a chain or ring to which the carboxyl groups are attached. The carboxyl groups are not included when determining the number of carbon atoms in the chain or ring (e.g., 1,2,3 propane tricarboxylic acid would be considered to be a $C_3$ polycarboxylic acid containing three carboxyl groups and 1,2,3,4 butanetetracarboxylic acid would be considered to be a $C_4$ polycarboxylic acid containing four carboxyl groups). $C_2$-$C_9$ polycarboxylic acids include, but are not limited to aliphatic, aromatic, and alicyclic acids, either saturated or olefinically unsaturated, with at least two carboxyl groups per molecule. In some embodiments, aliphatic polycarboxylic acids may include a hydroxyl group attached to a carbon atom alpha to a carboxyl group (an α-hydroxy polycarboxylic acid). α-hydroxy polycarboxylic acids include citric acid (also known as 2-hydroxy-1,2,3 propane tricarboxylic acid) and tartaric acid.

Examples of specific polycarboxylic acids include, but are not limited to, oxalic acid, malonic acid, succinic acid, glutaric acid, adipic acid, maleic acid, fumaric acid, malic acid, pimelic acid, nonanedioic acid, dodecanedioic acid, octanedioic acid, phthalic acid, isophthalic acid, terephthalic acid, citraconic (methylmaleic acid), citric acid, tartaric acid, itaconic acid (methylenesuccinic acid), 1,2,3 propane tricarboxylic acid, transaconitic acid (trans-1-propene-1,2,3 -tricarboxylic acid), 1,2,3,4-butanetetracarboxylic acid, all-cis-1,2,3,4-cyclopentanetetracarboxylic acid, mellitic acid (benzenehexacarboxylic acid), oxydisuccinic acid (2,2'-oxybis(butanedioic acid), α-bromoglutaric acid, 3,3-dimethylpentanedioic acid, and 2,4-dicholoropentanedioic acid.

Bioadhesive polymers include polyethylene oxide, KLUCEL (hydroxypropylcellulose), CARBOPOL, polycarbophil, GANTREZ, Poloxamer, and combinations thereof, and others known to one of ordinary skill in the art.

Retardants are agents that are insoluble or slightly soluble polymers with a Tg above 45° C., or above 50° C. before being plasticized by other agents in the formulation including other polymers and other excipients needed for processing. The excipients include waxes, acrylics, cellulosics, lipids, proteins, glycols, and the like.

Exemplary pore formers include water soluble polymers such as polyethylene glycol, propylene glycol, and povidone; binders such as lactose, calcium sulfate, calcium phosphate and the like; salts such as sodium chloride, magnesium chloride and the like, poloxamers and combinations thereof and other similar or equivalent materials which are widely known in the art. Examples of poloxamers include, but are not limited to: Pluronic® F-68 (Poloxamer 188), Pluronic® F87 (Poloxamer 237), Pluronic® F108 (Poloxamer 338), Pluronic® F127 (Poloxamer 407, Lutrol F127) and the like. Pluronic® is a registered tradename for BASF Corporation for block copolymers of ethylene oxide and propylene oxide represented by the chemical structure $HO(C_2H_4O)_a(C_3H_6O)_b(C_2H_4O)_aH$ wherein for: (a) Pluronic® F-68, a is 80 and b is 27; (b) Pluronic® F87, a is 64 and b is 37; (c) Pluronic® F108, a is 141 and b is 44; and Pluronic® F127, a is 101 and b is 56. The average molecular weights of these block copolymers are 8,400, 7,700, 14,600 and 12,600 for Pluronic® F-68, Pluronic® F-87, Pluronic® F108 and Pluronic® F127, respectively.

Exemplary osmagents or osmotic agents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol, sucrose, fructose and other such materials known to those of ordinary skill in the art.

It should be understood that compounds used as excipients or that are used to modify the oral dosage form, may serve a variety of functions or purposes. Thus, whether a compound named herein is assigned to one or more classifications or functions, its purpose or function should not be considered as being limited to the named purpose or function.

In one embodiment, an oral dosage form includes a progestogen dispersed in an enteric polymer combined with an estrogen. In an embodiment, the oral dosage form may include particles of a progestogen dispersed in an enteric polymer combined with an estrogen. The enteric polymer dispersed progestogen particles and estrogen may be dispersed in a monolithic, solidified enteric polymer. Alternatively, the enteric polymer dispersed progestogen particles and estrogen may be combined to form a tablet using suitable binders. The oral dosage form may include between about 0.5 mg to about 50 mg of a progestogen and between about 0.01 mg to about 1.0 mg of an estrogen.

The enteric polymer dispersed progestogen particles may be formed by mixing together one or more enteric polymers, the progestogen, and one or more optional plasticizers or excipients. The enteric polymer may represent between about 20% to about 99.9% of the mixture. The resulting mixture is heated. Preferably, the mixture is heated to a temperature above the glass transition point of the enteric polymer, as modified any plasticizers or excipients that, optionally, have been added to the mixture. The resulting heated mixture is allowed to solidify as a solid mass. The solid mass may be used to form the enteric polymer dispersed progestogen particles.

The mixture of the enteric polymer, progestogen, estrogen derivative and any optional plasticizers or excipients can be formed by any suitable means. Well-known mixing means known to those skilled in the art include dry mixing, dry granulation, wet granulation, melt granualation, high shear mixing, low shear mixing, and supercritical fluid processes.

Granulation generally is the process wherein particles of powder are made to adhere to one another to form granules, typically in the size range of 0.2 to 4.0 mm. Granulation methods are generally preferred in pharmaceutical formulations because they produce relatively homogeneous mixing of different sized particles.

A dry granulation process is used to form granules without using a liquid solution. Dry granulation may be conducted on a press using slugging tooling or on a roller compactor commonly referred to as a chilsonator.

Wet granulation involves forming granules using a granulating fluid or wetting agent that is subsequently removed by drying. For progestogens and enteric polymers, a wetting fluid may be an organic solvent having a boiling point of less than about 100° C. Examples of suitable solvents include, but are not limited to, acetone, methanol, ethanol, ethyl ether, ethyl acetate, chlorinated solvents, or mixtures thereof. The enteric polymer and the solubilized or suspended progestogen may be introduced into a granulator. Granulators can be low shear, medium shear, or high shear. Shear is the amount of mechanical force of the granulator. A low-shear granulator uses very little mechanical force to combine powders and binding solution. The fluid-bed granulator, the most commonly used low-shear granulator, uses a high volume of air flow to elevate powders in a chamber while the solution/suspension that contains the active agent(s) is sprayed onto the enteric polymer particles to form a light bond. A fluid-bed granulator does not impart mechanical energy but instead relies on the powder characteristics and the binding solution to form the lightly held powders into granules. After the granulation process is completed, the resulting mixture may be dried to remove at least a portion of the solvent.

In an alternate embodiment, an organic solvent having a boiling point that is greater than 100° C. may be used in a wet granulation process. Examples of such solvents that are suitable for use with progestogens include, but are not limited to: poloxamers, glycerin, triethyl citrate, dibutyl sebacate, triacetin, olive oil, propylene glycol, castor oil, or combinations thereof. The enteric polymer and the solubilized or suspended progestogen may be introduced into a granulator. The resulting mixture may be used directly to form an oral dosage form, without a drying step. The solvent used to dissolve/suspend the mixture may be incorporated into the oral dosage form during subsequent processing.

In an alternate embodiment, an organic solvent having a boiling point that is greater than 100° C. may be used to introduce the progestogen into an extruder. Thus, an enteric polymer may be introduced into an extruder and heated to a temperature at or above the glass transition temperature of the enteric polymer. The solubilized or suspended progestogen may be introduced into the extruder after the enteric polymer is heated. In one embodiment, the solubilized or suspended progestogen may be introduced at a point proximate to the exit of the extruder to minimize the amount of time the active ingredients are exposed to the heated polymer. The solvent used to dissolve/suspend the mixture may be incorporated into the oral dosage form during the extrusion process.

Melt granulation is a process in which powders are transformed into solid aggregates or agglomerates while being heated. It is similar to wet granulation except that a binder acts as a wetting agent only after it has melted. All of these and other methods of mixing pharmaceutical formulations are well-known in the art.

In certain embodiments, a mixture of the enteric polymer, progestogen, estrogen derivative and any optional plasticizers or excipients may be formed by producing a mixture of the selected components in a supercritical fluid and removing the supercritical fluid. In some embodiments the supercritical fluid is carbon dioxide or others known in the art.

In some embodiments, the progestogen may be in a micronized form. Micronized progestogens comprise particles having an average particle size of less than about 50 µm. The micronized progestogen may be combined with an enteric polymer to form a mixture suitable for further processing. In some embodiments, the enteric polymer may also be in a micronized from (i.e., enteric polymer particles have an average particle size of less than about 50 µm)

In some embodiments milling of one or more of the components may be performed to reduce or homogenize the particle size of the components. Techniques that may be used for reducing or homogenize the component particles include, but are not limited to, impact milling, attrition milling, knife milling, and direct-pressure milling.

Impact milling occurs when a hard object that applies a blunt force across a wide area hits a particle to fracture it. This milling action may be produced by a rotating assembly that uses blunt or hammer-type blades. Another type of impact mill is a jet mill. A jet mill uses compressed gas to accelerate the particles, causing them to impact against each other in the process chamber. Impact mills can reduce both fine powders and large chunks of friable material down to average particle sizes of 50 µm with mechanical impact mills, and less than 10 µm with jet mills. Mechanical impact mill types include hammermills, pin mills, cage mills, universal mills, and turbo mills.

In attrition milling, nondegradable grinding media continuously contacts the material, systematically grinding its edges down. This milling action is typically produced by a horizontal rotating vessel filled with grinding media and tends to create free-flowing, spherical particles. Attrition mills can reduce materials down to an average particle size of less than 1 µm. One type of attrition mill is the media mill (also called a ball mill).

In knife milling, a sharp blade applies high, head-on shear force to a large particle, cutting it to a predetermined size to create smaller particles and minimize fines. This milling action is produced by a rotating assembly that uses sharp knives or blades to cut the particles. Knife mills can reduce 2-inch or larger chunks or slabs of material down to 250 to 1,200 µm. Mill types include knife cutters, dicing mills, and guillotine mills.

Direct-pressure milling occurs when a particle is crushed or pinched between two hardened surfaces. Two rotating bars or one rotating bar and a stationary plate generally produce this milling action. Direct-pressure mills typically reduce friable materials down to 800 to 1,000 µm. Types include roll mills, cracking mills, and oscillator mills.

Subsequent or simultaneous with mixing, the mixture of enteric polymer, progestogen, and optional plasticizer and excipients is heated to produce a mass sufficiently fluid to permit shaping of the mixture and/or to produce melding of the components of the mixture. The heated mixture is then permitted to solidify as a substantially solid oral dosage form. The mixture can optionally be shaped or cut into suitable sizes during the heating step or during the solidifying step.

For purposes of the present disclosure a mixture is "heated" by applying thermal or mechanical energy to the mixture. In some embodiments, the mixture may be heated to a temperature such that the mixture is partially or substantially completely molten. For instance, in a mixture that includes an enteric polymer, "melting" the mixture may include substantially melting the enteric polymer without substantially melting one or more other materials present in the mixture (e.g., the therapeutic agent and one or more excipients). Generally, a mixture is sufficiently molten, for example, when it can be extruded as a continuous rod, or when it can be subjected to injection molding.

In preferred embodiments, the mixture becomes a homogeneous mixture either prior to or during the heating step.

Methods of heating the mixture include, but are not limited to, hot-melt extrusion, injection molding and compression molding.

Hot-melt extrusion typically involves the use of an extruder device. Such devices are well-known in the art. Such systems include mechanisms for heating the mixture to an appropriate temperature and forcing the heated feed material under pressure through a die to produce a rod, sheet or other desired shape of constant cross-section. Subsequent to, or simultaneous with, being forced through the die, the extrudate can be cut into smaller sizes appropriate for use as an oral dosage form. Any suitable cutting device known to those skilled in the art can be used, and the mixture can be cut into appropriate sizes either while still at least somewhat soft or after the extrudate has solidified. The extrudate may be cut, ground or otherwise shaped to a shape and size appropriate to the desired oral dosage form prior to solidification, or may be cut, ground or otherwise shaped after solidification. In some embodiments, an oral dosage form may be made as a non-compressed hot-melt extrudate.

Under certain conditions, extrusion of a composition may result in "die-swelling," a phenomenon in which the extrudate swells diametrically after exiting the die. In certain embodiments, die-swelling can be desirable, producing an extrudate having greater porosity and thus accelerated release characteristics. In other embodiments, it can be desirable to avoid die swelling, thereby producing a more solid composition that has slower therapeutic release and/or is slower to dissolve in a solvent such as aqueous ethanol solutions and/or is harder.

Injection molding typically involves the use of an injection-molding device. Such devices are well-known in the art. Injection molding systems force a melted mixture into a mold of an appropriate size and shape. The mixture solidifies as least partially within the mold and then is released.

Compression molding typically involves the use of an compression-molding device. Such devices are well-known in the art. Compression molding is a method in which the mixture is optionally preheated and then placed into a heated mold cavity. The mold is closed and pressure is applied. Heat and pressure are typically applied until the molding material is cured. The molded oral dosage form is then released from the mold.

An oral dosage form produced by a thermal process may exhibit low moisture content. Reduced moisture content of the oral dosage form may improve the stability of the oral dosage form, thus extending the shelf life of the oral dosage form. In one embodiment, the oral dosage form has a moisture content of less than 5%, less than 4%, less than 3%, less than 2%, or less than 1%.

The final step in the process of making oral dosage forms is permitting the oral dosage form as a substantially solid oral dosage form. The oral dosage form may optionally be shaped either prior to solidification or after solidification of the dosage form. Solidification will generally occur either as a result of cooling of the melted mixture or as a result of curing of the mixture however any suitable method for producing a solid dosage form may be used.

In certain embodiments, prior to administration the substantially solid oral dosage form may be cut, ground or otherwise shaped into its final form, or may be allowed to remain in its final molded configuration. Optionally the substantially solid oral dosage form can further include one or more coatings, including polymeric coatings and the like.

In one embodiment, an oral dosage form may include progestogen particles and particles of an estrogen derivative compressed into a tablet. The tablet form may include between about 0.5 mg to about 50 mg of enteric polymer dispersed progestogen particles and between about 0.01 mg to about 1.0 mg of an estrogen.

The progestogen particles may be combined with particles of an estrogen to form a tablet. A mixture of progestogen particles and an estrogen may be formed by using any type of granulation process, such as the processes described above, or other mixing techniques known in the art. In one embodiment, the progestogen and/or the estrogen may be in micronized form. In an embodiment, an inactive ingredient, usually referred to as a binder, is added to the mixture of progestogen particles and estrogen particles to help hold the tablet together and give it strength. A wide variety of binders may be used and are well known in the art. Binders include, but are not limited to: lactose powder, dibasic calcium phosphate, sucrose, corn (maize) starch, microcrystalline cellulose and modified cellulose (for example hydroxymethyl cellulose). After mixing is complete, the tablet formulation may be placed in a tablet press and compressed to form a tablet.

In some embodiments, disintegrants may be added to the tablet formulation that hydrates readily in water to aid tablet dispersion once swallowed. Some binders, such as starch and cellulose, are also excellent disintegrants. Small amounts of lubricants may be added to the tablet formulation, as well.

Examples of lubricants are well known in the art and include, but are not limited to: magnesium stearate, stearic acid (stearin), hydrogenated oil, and sodium stearyl fumarate. Lubricants help the tablets, once pressed, to be more easily ejected from the die.

A coating may be formed on the tablet. Examples of coating include enteric coatings, immediate release coatings, or extended release coatings. In some embodiments, an enteric coating may be formed over the oral dosage form. An enteric coating may be formed from a cellulose based enteric polymer, a vinyl based enteric polymer, or an acrylic acid—methacrylic acid based enteric polymer.

In another embodiment, enteric polymer dispersed progestogen particles may be combined with particles of an estrogen to form a tablet. The enteric polymer dispersed progestogen particles may be formed by mixing together one or more enteric polymers and a progestogen as described above. The resulting mixture is heated, preferably to a temperature above the glass transition point of the enteric polymer, as modified any plasticizers or excipients that, optionally, have been added to the mixture and formed into a solid mass. The solid mass may be subjected to a grinding and/or milling process to create enteric polymer dispersed progestogen particles. In an alternate method, the resulting heated mixture may be passed through an extruder under conditions such that an extrudate is produced having a length of no more than 1 mm. In an embodiment, the enteric polymer dispersed progestogen particles, produced by either method, have an average particle size of between about 100 μm and about 700 μm, between about 200 μm and about 600 μm, or between about 300 μm and about 400 μm. A mixture of progestogen particles and an estrogen may be formed into a tablet as described above.

In another embodiment, an oral dosage form may include enteric polymer dispersed progestogen particles compressed into a tablet and an estrogen dispersed in a coating layer formed over the tablet. Coatings may be formed from one or more hydrophilic polymers, hydrophobic polymers or enteric polymers. A coating may be formed by a spray coating process, where the polymer and estrogen are dissolved in a solvent and sprayed onto the progestogen containing tablet. The resulting oral dosage form includes enteric polymer dispersed progestogen particles in a tablet form and a coating layer that includes an estrogen dispersed in a polymeric coating material. In an embodiment, the coating may be formed from a mixture of the estrogen in an enteric polymer.

In another embodiment, an oral dosage form includes a progestogen dispersed in an enteric polymer as a monolithic, solidified form and an estrogen formed in a coating layer over the monolithic, solidified form. A monolithic, solidified enteric polymer that includes a progestogen may be formed by mixing together one or more enteric polymers and a progestogen as described above. The resulting mixture is heated, preferably to a temperature above the glass transition point of the enteric polymer, as modified any plasticizers or excipients that, optionally, have been added to the mixture. The resulting heated mixture is allowed to solidify as a solid mass.

A coating that includes an estrogen may be formed on the monolithic, solidified progestogen enteric polymer. Coatings may be formed from one or more hydrophilic polymers, hydrophobic polymers or enteric polymers. A coating may be formed by a spray coating process, where the polymer and estrogen are dissolved in a solvent and sprayed onto the progestogen containing oral dosage form. The resulting oral dosage form includes enteric polymer dispersed progestogen particles in a monolithic, solidified form and a coating layer that includes an estrogen dispersed in a polymeric coating material. In an embodiment, the coating may be formed from a mixture of the estrogen in an enteric polymer.

In another embodiment, an oral dosage form includes a progestogen and an estrogen dispersed in an enteric polymer. In an embodiment, the progestogen and estrogen derivative may be dispersed in a monolithic, solidified enteric polymer. A monolithic, solidified enteric polymer that includes a progestogen and an estrogen may be formed by mixing together one or more enteric polymers, the progestogen and the estrogen. The mixture may, optionally, include one or more plasticizers or one or more excipients. The enteric polymer may represent between about 20% to about 99.9% of the mixture. The resulting mixture is heated. Preferably, the mixture is heated to a temperature above the glass transition point of the enteric polymer, as modified any plasticizers or excipients that, optionally, have been added to the mixture. The resulting heated mixture is allowed to solidify as a solid mass. The solid mass may be used directly to form the oral dosage form or may, optionally, be shaped into a form for use as an oral dosage form. An enteric coating, immediate release coating, or extended release coating may be formed on the monolithic, solidified oral dosage form.

The monolithic, solidified oral dosage forms may be formed in any size suitable for oral administration. In some embodiments, oral dosage forms are roughly cylindrical in shape. In a plane perpendicular to the long axis of the cylinder the roughly cylindrical preferred oral dosage form has a diameter of 5 mm or greater, 6 mm or greater, 7 mm or greater, 8 mm or greater, 9 mm or greater, or 10 mm or greater. Along the long axis of the cylinder the preferred oral dosage form has a length of 1, 2, 3, 4, 5, 6, 7, 8, 9, 10, 11, 12, 13, 14 or 15 mm or greater. Such dosage forms could be formed, for example, by extruding the oral dosage form through a die that is at least 0.5 mm in diameter, 0.6 mm in diameter, 0.7 mm, etc., in diameter and then cutting the extrudate to a length of 1, 2, 3, 4, 5 mm, etc., in length.

The compositions described herein are suitable for immediate release, controlled release and extended release applications, or combinations thereof, depending on the types of polymers, plasticizers and excipients used and their proportions. Methods for adjusting these characteristics will be apparent to those skilled in the art or can be determined without undue experimentation. For example, immediate release characteristics of the oral dosage forms may be enhanced by the inclusion of hydrophilic polymers, plasticizers and/or excipients to enhance the formation of pores in the oral dosage form, particularly those that begin forming when the oral dosage form is subjected to gastric conditions. Alternatively, immediate release characteristics may be suppressed, for example, by coating the oral dosage form with a suitable enteric coating that does not contain the therapeutic agent. By adjusting variables such as these, a range of release characteristics can be obtained from the oral dosage forms.

In some embodiments, the oral dosage form may be disposed in a capsule. In one embodiment, a monolithic solid oral dosage form may be disposed in a capsule. In other embodiments, enteric polymer dispersed progestogen particles and particles of an estrogen may be disposed in a capsule. Examples of materials that may be used to encapsulate the oral dosage form include, but are not limited to, gelatin capsules, hydroxypropylmethyl cellulose ("HPMC") capsules, or polysaccharide capsules (e.g., pullulan capsules).

In one embodiment, the oral dosage forms disclosed herein may be used to produce a contraceptive state in a subject. The method of achieving such a state includes administering, to said subject, on each day of at least 21 consecutive days, a daily oral dosage unit, prepared according to any of the embodiments described herein, that includes a progestogen compound described herein. The method further includes administering, on each day of 7 or less consecutive days, a daily dosage unit containing no active agent, or alternatively, administering no dosage units for 7 days or less.

In another embodiment, the oral dosage forms disclosed herein may be used to produce a contraceptive state in a subject. The method of achieving such a state includes administering, to said subject, on each day of at least 21 consecutive days, a daily oral dosage unit, prepared according to any of the embodiments described herein, that includes a combination of a progestogen and an estrogen. The method further includes administering, on each day of 7 or less consecutive days, a daily dosage unit containing no active agent, or alternatively, administering no dosage units for 7 days or less.

In suitable embodiments of this method, the daily dosage units including a combination of a progestogen and an estrogen may be administered for 21, 22, 23 or 24 consecutive days, and the daily dosage units containing no active agent may then be administered for 7, 6, 5 or 4 consecutive days, as appropriate. Furthermore, the daily dosage units including the combination of a progestogen and an estrogen derivative may be administered for 28-168 consecutive days.

Alternatively, the present method includes administering, on each day of at least 21 consecutive days, a daily dosage unit that includes a combination of a progestogen and an estrogen, followed by administering, on each day of 7 or less consecutive days, a daily dosage unit containing an estrogen alone in an amount of from about 0.01 mg to about 1.0 mg. Oral dosage forms of an estrogen may be formed by hot-melt extrusion, as described above or any of known tableting procedures.

In this alternative method, the daily dosage units that include a combination of a progestogen and an estrogen may suitably be administered for 21, 22, 23 or 24 consecutive days, and the daily dosage units that include an estrogen alone may then be administered for 7, 6, 5 or 4 consecutive days, as appropriate.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

2,2-Ethylene-6β,7β:15β,16β-dimethylene-3-oxo-17α-pregn-4-ene-21,17-carbolactone (IIIe)

To a solution of trimethylsulfoxonium iodide (337 mg, 1.53 mmol) in DMSO (4.0 mL) was added sodium hydride (60% oil suspension; 58 mg, 1.46 mmol) and the mixture stirred vigorously under nitrogen at ambient temperature. After 30 minutes, a solution of 3-oxo-2:6β,7β:15β,16β-trimethylene-17α-pregn-4-ene-21,17-carbolactone [Nickisch et al., *J. Med. Chem.,* 1985, 28, 546] (460.7 mg, 1.22 mmol) in DMSO (8.0 mL) was added dropwise over a period of 10 minutes. Upon completion of addition, stirring was continued one hour at ambient temperature. At that time, all starting material had been converted to a single product as evidenced by thin layer chromatography (tlc; silica, 50:50 ethyl acetate: hexanes). The reaction was diluted with water and extracted into ethyl acetate (3×). Ethyl acetate extracts were washed further with water and brine, dried over sodium sulfate and evaporated in vacuo to afford crude product (0.54 g). Purification by flash chromatography (silica; 10% acetone in methylene chloride) provided the purified 2,2-cyclopropyl derivative (IIIe) as a foam (420.3 mg, 1.07 mmol, 87.7%). Crystallization from acetone/hexanes afforded off-white needles. m.p. 190.8-195.9° C. IR 1762, 1659, 1646, 1593 cm$^{-1}$. NMR 0.983 (C-18), 1.151 (C-19), 6.101 (C-4) ppm.

EXAMPLE 2

1α,2α:15β,16β-Dimethylene-6,6-ethylene-3-oxo-17α-pregn-4-ene-21,17-carbolactone (IVe)

A solution of trimethylsulfoxonium iodide (3.91 g, 17.75 mmol) in DMSO (35 mL) is added to sodium hydride (60% oil suspension; 667 mg, 16.65 mmol) and the mixture stirred vigorously at ambient temperature, under nitrogen. After one hour, a solution of 6,6-ethylene-15β,16β-methylene-3-oxo-17α-pregna-1,4-diene 21,17-carbolactone [Nickisch et al., *J. Med. Chem.*, 1991, 34, 2464] (840 mg, 2.22 mmol) in DMSO (8.0 mL) was added and stirring continued at 65° C. for 5 hours. The reaction mixture was cooled to room temperature and poured slowly into ice water. The mixture was made slightly acidic with dilute sulfuric acid and extracted with dichloromethane (3×). The organic fractions were washed with water (2×), brine (1×), combined, dried over anhydrous Na$_2$SO$_4$ and concentrated in vacuo to give 1.03 g of a brown oil. Chromatographic purification on silica gel (5% acetone/dichloromethane) followed by crystallization from acetone/hexanes gave the pure 1,2-cyclopropyl product (IVc, 0.405 g, 46.9%). m.p. 216-217° C. IR 2923, 2850, 1758, 1655, 1612 cm$^{-1}$. NMR 0.452, 0.852, 1.066 (C-18), 1.372 (C-19), 5.417 (C-4) ppm. MS (EI): 392 (M$^+$).

The following assays have been used in assessing the value of compounds of formulas (I) and (II) for use in contraceptive and hormone replacement therapy products.

Androgen Receptor Binding Assay: To screen for compounds with affinity for the androgen receptor (AR), an AR binding is performed using a recombinant AR as receptor source and the synthetic androgen methyltrienolone (R 1881). The relative affinity of test substances for the androgen receptor was taken as a measure of androgen antagonist activity and of the potential for anti-androgen side effects. Briefly, this assay involves competitive binding to recombinant rat androgen receptor ligand binding domain (ARLBD) using [$^3$H]-R1881. Different concentrations (e.g., 10 nM, 15 nM or 30 nM) of purified recombinant ARLBD are immobilized to an OptiPlate 96-well microtiter plate (Packard) via incubation at 4° C. in 100 μl/well PBS containing ARLBD. Following overnight incubation, solutions in the plates are aspirated and washed three times with PBS before the addition of increasing concentrations of the "test compound" (e.g., 0.5 to 500 nM) in presence of 5 nM [$^3$H]-R1881 in binding buffer. Non-specific binding was measured in the presence of 200-fold molar excess of unlabeled R1881. "No compound" controls contain DMSO/binding buffer without compound. The plates are incubated overnight at 4° C., after which solutions in the plates are aspirated and washed six times with PBS, followed by the addition of MicroScint-20 scintillation cocktail (Packard). The plates are sealed using transparent sealing tape and counted for radioactivity by use of the scintillation counter. The data thus obtained is used to determine the IC50 values and the relative binding affinity ("RBA") of the androgen receptor for the test compound.

Progestin Receptor Binding Assay: To screen for compounds with affinity for the progesterone receptors A and B, a binding assay is performed using recombinant human progesterone receptors A and B as receptor source and [$^3$H]-progesterone as the standard. Briefly, different concentrations (e.g., 10 nM, 15 nM or 30 nM) of purified recombinant human progesterone receptors A and B are immobilized to an OptiPlate 96-well microtiter plate (Packard) via incubation at 4° C. in 100 μl/well PBS containing ARLBD. Following overnight incubation, solutions in the plates are aspirated and washed three times with PBS before the addition of increasing concentrations of the "test compound" (e.g., 0.5 to 500 nM) in presence of 5 nM [$^3$H]-progesterone in binding buffer. Non-specific binding was measured in the presence of 200-fold molar excess of unlabeled progesterone. "No compound" controls contain DMSO/binding buffer without compound. The plates are incubated overnight at 4° C., after which solutions in the plates are aspirated and washed six times with PBS, followed by the addition of MicroScint-20 scintillation cocktail (Packard). The plates are sealed using transparent sealing tape and counted for radioactivity by use of the scintillation counter. The data thus obtained is used to determine the IC50 values and the RBA of the progesterone receptors A and B for the test compound.

TABLE 1

Binding of various compounds to hPR-A and hPR-B, hGR, and rat ARLBD.

| Compound | hPR-A | | hPR-B | | hGR | | ARLBD | |
|---|---|---|---|---|---|---|---|---|
| | IC$_{50}$ (nM) | RBA (%) | IC$_{50}$ (nM) | RBA (%) | IC$_{50}$ (nM) | RBA (%) | IC$_{50}$ (nM) | RBA (%) |
| Progesterone | 5.2 | 100 | 5.9 | 100 | | | | |
| R1881 | | | | | | | 2.9$^1$ | 100 |
| | | | | | | | 5.5$^2$ | 100 |
| | | | | | | | 4.2$^3$ | 100 |
| | | | | | | | 4.5$^4$ | 100 |
| Dexamethasone | | | | | 8.81 | 100 | | |
| | | | | | 9.42 | 100 | | |
| Drospirenone | 22.8 | 23 | 20.2 | 29 | >1000$^1$ | <0.9 | >1000$^1$ | <0.3 |
| | | | | | >1000$^2$ | <1.0 | >1000$^3$ | <0.5 |
| Compound (IIIe) | >1,000 | <0.6 | >1000 | <0.6 | >1000$^1$ | <0.9 | >1000$^2$ | <0.6 |
| | | | | | >1000$^2$ | <1.0 | >1000$^3$ | <0.5 |
| Compound (IVa) | 3.5 | 149 | 5.1 | 116 | 45.1$^1$ | 20 | 28.0$^2$ | 20 |
| | | | | | 64.0$^2$ | 15 | 17.7$^4$ | 25 |
| Compound (IVb) | 13.8 | 38 | 15.4 | 38 | 87.9$^1$ | 10 | 101.4$^2$ | 5 |
| | | | | | 120.6$^2$ | 8 | 107.9$^3$ | 4 |

TABLE 1-continued

Binding of various compounds to hPR-A and hPR-B, hGR, and rat ARLBD.

| Compound | hPR-A | | hPR-B | | hGR | | ARLBD | |
|---|---|---|---|---|---|---|---|---|
| | $IC_{50}$ (nM) | RBA (%) | $IC_{50}$ (nM) | RBA (%) | $IC_{50}$ (nM) | RBA (%) | $IC_{50}$ (nM) | RBA (%) |
| Compound (IVc) | 6.7 | 78 | 8.3 | 71 | $116.8^1$ | 8 | $83.6^2$ | 7 |
| | | | | | $299.6^2$ | 3 | $80.9^3$ | 5 |

[1,2,3,4]Values with the same superscript were from the same assay

Androgen Transactivation Assay: Transcriptional activity is assessed by transient co-transfection of CV 1 African green monkey kidney cells with a luciferase reporter vector containing three hormone response elements (progestin, glucocorticoid and androgen), 3XHRE-LUC and a human androgen receptor expression vector (pCMV5hAR3.1). The transfected cells are then treated with 10-13 different concentrations of the test compound. Cells are harvested in adequate amount of lysis buffer. Relative light units of a 0.1-ml aliquot are determined using a luminometer. The data thus obtained is used to estimate an EC50 for the test compound and to generate a dose response curve.

Figure 2:
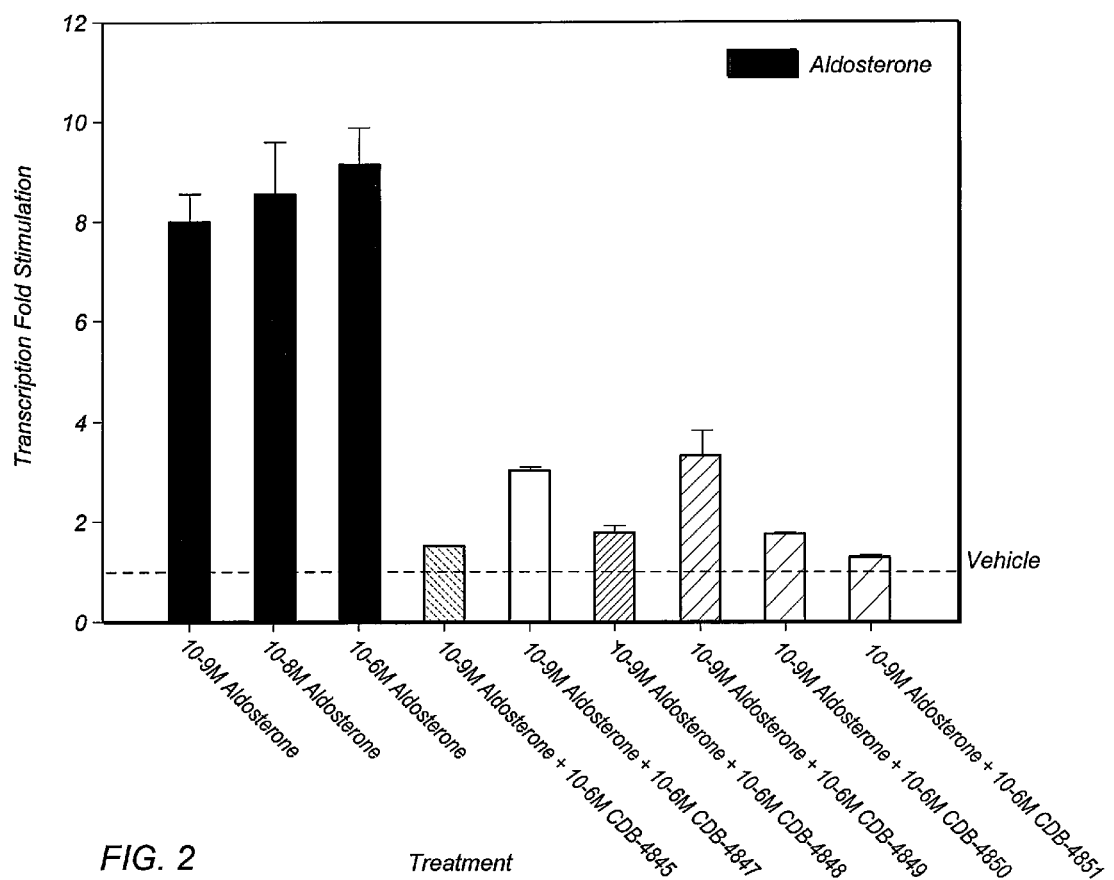
FIG. 2 depicts further results from the transient transfection of CV-1 Cells with 3XHRE-tk-LUC and a human mineralocorticoid expression vector (pchMR).

Mineralocorticoid Activity: Transient transfection of CV-1 cells, which lack endogenous steroid hormone receptors, with the 3XHRE-LUC reporter plasmid and human mineralocorticoid expression vector were carried out to determine whether the fine compounds CDB-4874, 4848, 4849, 4850, and 4851 demonstrate mineralocorticoid or antimineralocorticoid activity. Results from this testing is presented in FIGS. 1 and 2. The $IC_{50}$ for inhibition of aldosterone-stimulated transactivation by spironolactone was also determined. CV-1 cells were cotransfected with 3XHRE-LUC and pchMR at a ratio of 1:1.

I. Experimental Materials and Procedures
  A. Cells: CV-1 cells prepared in MEMα without phenol red+10% Hyclone DCC-stripped FBS+1% penicillin/streptomycin+25 mM HEPES. Plate @~$0.2 \times 10^6$ cells/well in 6-well FALCON plates one day before transfection using a 10-ml pipette while cells are on a stirring motor.
  B. Plasmids
    1. pGL3-LUC diluted to 1.0 µg/µl
    2. pchMR diluted to 1.0 µg/µl
    3. 3XHRE-tk-LUC diluted to 1.0 µg/µl
  C. Transfection Reagent
    1. FuGENE 6
  D. Laboratory Procedures
    1. Before starting transfection, aspirate and discard medium, and add 2 ml fresh medium containing 10% Hyclone DCC-stripped FBS+1% pen/strep. Transfect at the ratio of 6:1 (reagent: DNA, µl:µg). Duplicate wells of cells will be incubated for 6 h with FuGENE 6-DNA complexes as indicated in Table 2 and washed once with 2 ml DPBS. Fresh medium containing ethanol vehicle or CDB compounds in ethanol will be added as indicated in Table 2.
    2. Add the amount of FuGENE 6 Regent indicated in Table 2 directly into serum- and pen/strep-free MEMα to a total volume of 100 µl/well. Use sterile 12×75 mm or 17×100 mm polypropylene tubes, as appropriate. Do not allow reagent to come into contact with any plastic surface other than the pipette tip.
    3. Add DNA solution in a total volume of 0.5-50 µl/100 µl. Gently tap the tube to mix the contents. Do not vortex. Incubate for 45 min at room temperature. Stagger start of incubation mixtures by ~20 min.
    4. Mix transfection mixtures gently by hand at the beginning of each series, and do not mix again. Add 100 µl of the complex dropwise to all wells while swirling to distribute it evenly around the cells. After mixtures have been added to all 6 wells in the plate, swirl plate again. Incubate cells at 37° C. and 5% $CO_2$ for 6 h.
    5. Wash cells once with 2 ml DPBS, and add 2 ml fresh medium containing CDB compounds or vehicle as indicated in Table 3. Add $10^{-6}$M aldosterone to medium to $10^{-9}$ M, and distribute to tubes as indicated in Tables 3a and 3c.
    6. Return plates to incubator. Incubate overnight at 37° C. and 5% $CO_2$. Note confluence and appearance of cells.
    7. Harvest cells after 20 h as described below. Completely remove the growth medium. Wash surface of the cells gently with 2 ml DPBS, swirl, and remove completely. Add to each culture well 100 µl 1× Passive Lysis Buffer. Incubate for 15 min at room temperature. Scrape cells with a disposable cell scraper, and transfer lysate to microfuge tube. Clear lysates by centrifugation in a microfuge for 2 min at maximum speed. Transfer supernatants to another series of microfuge tubes or cryovials. Remove as much supernatant as possible without removing pellets which may be loose. Store cell lysates at −70° C.
    8. Measure luciferase activity and protein concentration using the Biorad Bradford assay.

TABLE 2

Transfection Mixtures for CV-1 Cells

| Wells | MEMα (µl) | FuGENE 6 (µl) | DNA (µl) | Medium (MEMα) |
|---|---|---|---|---|
| 1, 2 | 197 | 12.6 | 2.1 µg pGL3 (2.1 µl) | EtOH |
| 3, 4 | 2726 | 174 | 29 µg 3XHRE-LUC | EtOH |
| 5, 6 | | | (29 µl @ 1 µg/µl) + 29 µg pchMR (29 µl @ 1 µg/µl) | $10^{-9}$ M aldosterone (CDB 3338A) |
| 7, 8 | | | Ratio 1:1 | $10^{-8}$ M aldosterone |
| 9, 10 | | | | $10^{-6}$ M aldosterone |
| 11, 12 | | | | $10^{-9}$ M aldosterone + $10^{-6}$ M spironolactone (CDB-4845) |
| 13, 14 | | | | $10^{-9}$ M aldosterone + $10^{-6}$ M CDB 4847 |

TABLE 2-continued

Transfection Mixtures for CV-1 Cells

| Wells | MEMα (μl) | FuGENE 6 (μl) | DNA (μl) | Medium (MEMα) |
|---|---|---|---|---|
| 15, 16 | | | | $10^{-9}$ M aldosterone + $10^{-6}$ M CDB 4848 |
| 17, 18 | | | | $10^{-9}$ M aldosterone + $10^{-6}$ M CDB 4849 |
| 19, 20 | | | | $10^{-9}$ M aldosterone + $10^{-6}$ M CDB 4850 |
| 21, 22 | | | | $10^{-9}$ M aldosterone + $10^{-6}$ M CDB 4851 |
| 23, 24 | | | | $10^{-9}$ M CDB-4847 |
| 25, 26 | | | | $10^{-8}$ M CDB-4847 |
| 27, 28 | | | | $10^{-6}$ M CDB-4847 |
| 29, 30 | | | | EtOH |
| 31, 32 | 2726 | 174 | 29 μg 3XHRE-LUC (29 μl @ 1 μg/μl) + 29 μg pchMR (29 μl @ 1 μg/μl) Ratio 1:1 | EtOH |
| 33, 34 | | | | $10^{-9}$ M CDB-4848 |
| 35, 36 | | | | $10^{-8}$ M CDB-4848 |
| 37, 38 | | | | $10^{-6}$ M CDB-4848 |
| 39, 40 | | | | $10^{-9}$ M CDB-4849 |
| 41, 42 | | | | $10^{-8}$ M CDB-4849 |
| 43, 44 | | | | $10^{-6}$ M CDB-4849 |
| 45, 46 | | | | $10^{-9}$ M CDB-4850 |
| 47, 48 | | | | $10^{-8}$ M CDB-4850 |
| 49, 50 | | | | $10^{-6}$ M CDB-4850 |
| 51, 52 | | | | $10^{-9}$ M CDB-4851 |
| 53, 54 | | | | $10^{-8}$ M CDB-4851 |
| 55, 56 | | | | $10^{-6}$ M CDB-4851 |
| 57, 58 | | | | EtOH |
| 59, 60 | 2538 | 162 | 27 μg 3XHRE-LUC (31 μl @ 1 μg/μl) + 27 μg pchMR (27 μl @ 1 μg/μl) Ratio 1:1 | EtOH |
| 61, 62 | | | | $10^{-9}$ M aldosterone (CDB-3338A) |
| 63, 64 | | | | $10^{-9}$ M aldosterone + $10^{-11}$ M spironolactone (CDB-4845) |
| 65, 66 | | | | $10^{-9}$ M aldosterone + $10^{-10}$ M spironolactone |
| 67, 68 | | | | $10^{-9}$ M aldosterone + $3.16 \times 10^{-10}$ M spironolactone |
| 69, 70 | | | | $10^{-9}$ M aldosterone + $10^{-9}$ M spironolactone |
| 71, 72 | | | | $10^{-9}$ M aldosterone + $3.16 \times 10^{-9}$ M spironolactone |
| 73, 74 | | | | $10^{-9}$ M aldosterone + $10^{-8}$ M spironolactone |
| 75, 76 | | | | $10^{-9}$ M aldosterone + $3.16 \times 10^{-8}$ M spironolactone |
| 77, 78 | | | | $10^{-9}$ M aldosterone + $10^{-7}$ M spironolactone |
| 79, 80 | | | | $10^{-6}$ M aldosterone + $3.16 \times 10^{-7}$ M spironolactone |
| 81, 82 | | | | $10^{-9}$ M aldosterone + $10^{-6}$ M spironolactone |
| 83, 84 | | | | EtOH |

TABLE 3a

Preparation of Media for CV-1 Cells

| Wells | Medium (MEMα + indicated additions) | MEMα (ml) | MEMα + $10^{-9}$ M aldo (ml) | CDB compound (μl) |
|---|---|---|---|---|
| 1-4, 29-32, 57, 58 | EtOH | 22 | | 22 μl EtOH |
| 5, 6 | $10^{-9}$ M aldosterone (CDB-3338A) | | 5.0 | |
| 7, 8 | $10^{-8}$ M aldosterone | 5.0 | | 5.0 μl $10^{-5}$ M aldosterone |
| 9, 10 | $10^{-6}$ M aldosterone | 5.0 | | 5.0 μl $10^{-3}$ M aldosterone |
| 11, 12 | $10^{-9}$ M aldosterone + $10^{-6}$ M spironolactone (CDB-4845) | | 5.0 | 5.0 μl $10^{-3}$ M spironolactone |
| 13, 14 | $10^{-9}$ M aldosterone + $10^{-6}$ M CDB-4847 | | 5.0 | 5.0 μl $10^{-3}$ M CDB-4847 |
| 15, 16 | $10^{-9}$ M aldosterone + $10^{-6}$ M CDB-4848 | | 5.0 | 5.0 μl $10^{-3}$ M CDB-4848 |
| 17, 18 | $10^{-9}$ M aldosterone + $10^{-6}$ M CDB-4849 | | 5.0 | 5.0 μl $10^{-3}$ M CDB-4849 |

TABLE 3a-continued

Preparation of Media for CV-1 Cells

| Wells | Medium (MEMα + indicated additions) | MEMα (ml) | MEMα + $10^{-9}$ M aldo (ml) | CDB compound (μl) |
|---|---|---|---|---|
| 19, 20 | $10^{-9}$ M aldosterone + $10^{-6}$ M CDB-4850 | | 5.0 | 5.0 μl $10^{-3}$ M CDB-4850 |
| 21, 22 | $10^{-9}$ M aldosterone + $10^{-6}$ M CDB-4851 | | 5.0 | 5.0 μl $10^{-3}$ M CDB-4851 |
| 23, 24 | $10^{-9}$ M CDB-4847 | 5.0 | | 5.0 μl $10^{-6}$ M CDB-4847 |
| 25, 26 | $10^{-8}$ M CDB-4847 | 5.0 | | 5.0 μl $10^{-5}$ M CDB-4847 |
| 27, 28 | $10^{-6}$ M CDB-4847 | 5.0 | | 5.0 μl $10^{-3}$ M |

TABLE 3b

Preparation of Media for CV-1 Cells

| Wells | Medium (MEMα + indicated additions) | MEMα (ml) | CDB compound (μl) |
|---|---|---|---|
| 33, 34 | $10^{-9}$ M CDB-4848 | 5.0 | 5.0 μl $10^{-6}$ M CDB-4848 |
| 35, 36 | $10^{-8}$ M CDB-4848 | 5.0 | 5.0 μl $10^{-5}$ M CDB-4848 |
| 37, 38 | $10^{-6}$ M CDB-4848 | 5.0 | 5.0 μl $10^{-3}$ M CDB-4848 |
| 39, 40 | $10^{-9}$ M CDB-4849 | 5.0 | 5.0 μl $10^{-6}$ M CDB-4849 |
| 41, 42 | $10^{-8}$ M CDB-4849 | 5.0 | 5.0 μl $10^{-5}$ M CDB-4849 |
| 43, 44 | $10^{-6}$ M CDB-4849 | 5.0 | 5.0 μl $10^{-3}$ M CDB-4849 |
| 45, 46 | $10^{-9}$ M CDB-4850 | 5.0 | 5.0 μl $10^{-6}$ M CDB-4850 |
| 47, 48 | $10^{-8}$ M CDB-4850 | 5.0 | 5.0 μl $10^{-5}$ M CDB-4850 |
| 49, 50 | $10^{-6}$ M CDB-4850 | 5.0 | 5.0 μl $10^{-3}$ M CDB-4850 |
| 51, 52 | $10^{-9}$ M CDB-4851 | 5.0 | 5.0 μl $10^{-6}$ M CDB-4851 |
| 53, 54 | $10^{-8}$ M CDB-4851 | 5.0 | 5.0 μl $10^{-5}$ M CDB-4851 |
| 55, 56 | $10^{-6}$ M CDB-4851 | 5.0 | 5.0 μl $10^{-3}$ M CDB-4851 |

TABLE 3c

Preparation of Media for CV-1 Cells

| Wells | Medium (MEMα + indicated additions) | MEMα + $10^{-9}$ M aldo (ml) | CDB compound (μl) |
|---|---|---|---|
| 59, 60, 83, 84 | EtOH | 9.0 (no aldo) | 18 μl EtOH |
| 61, 62 | $10^{-9}$ M aldosterone (CDB-3338A) | 5.0 | 5.0 μl EtOH |
| 63, 64 | $10^{-9}$ M aldosterone + $10^{-11}$ M spironolactone (CDB-4845) | 5.0 | 5.0 μl $10^{-8}$ M spironolactone |
| 65, 66 | $10^{-9}$ M aldosterone + $10^{-10}$ M spironolactone | 5.0 | 5.0 μl $10^{-7}$ M spironolactone |
| 67, 68 | $10^{-9}$ M aldosterone + 3.16 × $10^{-10}$ M spironolactone | 5.0 | 5.0 μl 3.16 × $10^{-7}$ M spironolactone |
| 69, 70 | $10^{-9}$ M aldosterone + $10^{-9}$ M spironolactone | 5.0 | 5.0 μl $10^{-6}$ M spironolactone |
| 71, 72 | $10^{-9}$ M aldosterone + 3.16 × $10^{-9}$ M spironolactone | 5.0 | 5.0 μl 3.16 × $10^{-6}$ M spironolactone |
| 73, 74 | $10^{-9}$ M aldosterone + $10^{-8}$ M spironolactone | 5.0 | 5.0 μl $10^{-5}$ M spironolactone |
| 75, 76 | $10^{-9}$ M aldosterone + 3.16 × $10^{-8}$ M spironolactone | 5.0 | 5.0 μl 3.16 × $10^{-5}$ M spironolactone |
| 77, 78 | $10^{-9}$ M aldosterone + $10^{-7}$ M spironolactone | 5.0 | 5.0 μl $10^{-4}$ M spironolactone |
| 79, 80 | $10^{-6}$ M aldosterone + 3.16 × $10^{-7}$ M spironolactone | 5.0 | 5.0 μl 3.16 × $10^{-4}$ M spironolactone |
| 81, 82 | $10^{-9}$ M aldosterone + $10^{-6}$ M spironolactone | 5.0 | 5.0 μl $10^{-3}$ M spironolactone |

Glucocorticoid Receptor Binding Assay: The competitive binding of CDB-4847 (EC-100), 4848 (EC-102), 4849 (EC-200), 4850 (EC-201), and 4851 (EC-202) was measured using recombinant human glucocorticoid receptor (rhGR). Incubations were carried out in microplates using 400 fmol rhGR/well, 10 nM [$^3$H]dex, and dexamethasone (CDB-3972A) as the standard. DCC is added to the wells after incubation to separate bound and unbound radioligand using a repeater pipettor to reduce variability.

I. Experimental Procedures and Methods

A. Reagents
  1. Recombinant human GR: 8.6 pmol/mg, 80 pmol/ml.
  2. KEM buffer (10 mM KPO$_4$, pH 7.4, 0.1 mM EDTA, 20 mM Na$_2$MoO$_4$)
  3. KEMD buffer (KEM buffer+5 mM DTT, add DTT the day of assay)
  4. 6, 7 [$^3$H]Dexamethasone, 34 Ci/mmol
  5. CDB-3972 (dexamethasone), 4×$10^{-3}$ M in ethanol
  6. 5% Dextran-coated charcoal solution in DEM buffer B. Assay Method—Set Up on Ice.
  1. Dilute 4×$10^{-3}$ M CDB-3972 to 4×$10^{-5}$ M (40 μM) in KEMD for NSB. The final concentration will be 10 μM.
  2. Thaw the rhGR on ice. Do not vortex. Dilute rhGR 1:5 (80 pmol/ml) to 16.0 pmol/ml in KEMD. At 25 μl/tube, the final concentration will be 400 fmol/tube in KEMD.
  3. Prepare KEMD containing 10% ethanol. Dilute the compounds to be assayed in KEMD containing 10% ethanol to the working concentrations specified in Table 3.
  4. Prepare a 40 nM solution [$^3$H]Dex in KEMD containing 10% ethanol. The final concentration will be 10 nM.
  5. Set up the assay in microplates. Use 3 wells for total counts (no receptor), 3 NSB, 6 total binding, and triplicate wells for each concentration of dex or CDB compound. Use Table 4 as pipetting guide. Mix gently, and incubate overnight at 2-6° C.

TABLE 4

Compound dilutions

| CDB Compound | Working Concentration (nM) | Final Concentration (nM) |
|---|---|---|
| CDB-3972 (dex, standard) | 2, 4, 10, 20, 40, 100, 200 nM | 0.5, 1, 2.5, 5, 10, 25, 50 nM |
| CDB-4847, 4848 | 40, 100, 200, 400, 2,000, 4,000 nM | 10, 25, 50, 100, 500, 1,000 nM |
| CDB-4849, 4850, 4851 | 40, 100, 200, 400, 1,000, 2,000, 4,000 nM | 10, 25 50, 100, 250, 500, 1,000 nM |

TABLE 5

| | KEMD | KEMD + 10% EtOH | 40 μM CDB-3972 (NSB) | Dil. Std/Comp. | 40 nM [3H]Dex | Diluted rhGR | 5% DCC |
|---|---|---|---|---|---|---|---|
| Pipetting guide for rhGR (volumes in μl) | | | | | | | |
| Total Counts | 100 | 25 | — | — | 25 | — | — |
| NSB | 25 | — | 25 | — | 25 | 25 | 50 |
| Total Binding | 25 | 25 | — | — | 25 | 25 | 50 |
| Dil. Std/Comp | 25 | — | — | 25 | 25 | 25 | 50 |

6. The next morning, prechill the Jouan centrifuge with microplate rotor. Add 50 μl of 5% DCC in KEM to all but total counts using a repeater pipettor. Make sure the DCC is constantly mixed and thoroughly resuspended before adding to the wells.
7. Mix gently in the cold room for 5 min on plate shaker.
8. Centrifuge at 3,000 rpm in the Jouan centrifuge at 4° C. for 15 min.
9. Keeping the plates on ice, pipet 100 μl of the supernatants into 24-well plates, add 1 ml of Microscint PS, and seal the plates. Pre-incubate the plates for 10 min in the counter, and count each well for 2 min in the TopCount.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An antimineralocorticoid compound having the structure of formula (I):

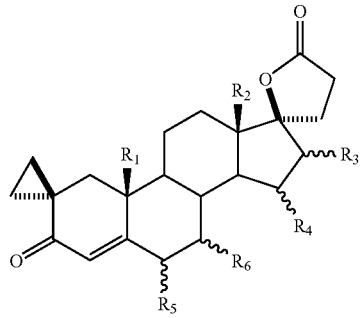

where: $R_1$ is H or $CH_3$;
$R_2$ is $CH_3$ or $CH_2CH_3$;
$R_3$ and $R_4$ are hydrogens; together form an α-$CH_2$ bridge between carbons 15 and 16; or together form a β-$CH_2$ bridge between carbons 15 and 16; and
$R_5$ and $R_6$ together form an α-$CH_2$ bridge between carbons 6 and 7 or a β-$CH_2$ bridge between carbons 6 and 7.

2. A progestogen compound having the structure of formula (II):

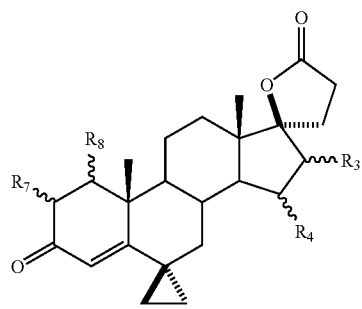

where:
$R_3$ and $R_4$ together form an α-$CH_2$ bridge between carbons 15 and 16 or a β-$CH_2$ bridge between carbons 15 and 16; and
$R_7$ and $R_8$ together form an α-$CH_2$ bridge between carbons 1 and 2.

3. The progestogen compound of claim 2, wherein $R_3$ and $R_4$ are a β-$CH_2$ bridge between carbons 15 and 16, the progestogen compound having the structure of formula (IVc):

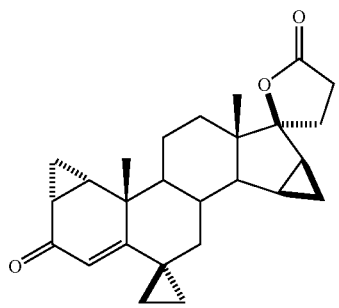

where $R_7$ and $R_8$ together form an α-$CH_2$ bridge between carbons 1 and 2.

4. An oral dosage form comprising a progestogen compound and one or more pharmaceutically acceptable carriers suitable for oral delivery of the progestogen compound, the progestogen compound having the structure of formula (II):

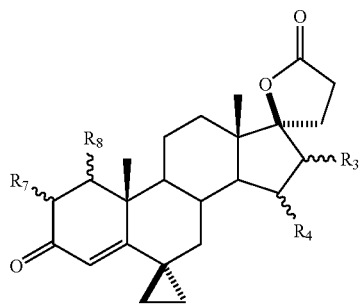

where:
R$_3$ and R$_4$ together form an α-CH$_2$ bridge between carbons 15 and 16 or a β-CH$_2$ bridge between carbons 15 and 16; and
R$_7$ and R$_8$ together form an α-CH$_2$ bridge between carbons 1 and 2.

5. The oral dosage form of claim 4, wherein the progestogen compound has the structure of formula (IVc):

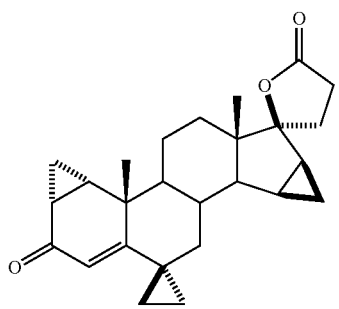

where R$_7$ and R$_8$ together form an α-CH$_2$ bridge between carbons 1 and 2.

6. The oral dosage form of claim 4, further comprising an estrogen compound.

7. The oral dosage form of claim 4, further comprising ethinylestradiol.

8. The oral dosage form of claim 4, wherein the oral dosage form is a tablet comprising particles of the progestogen compound.

9. The oral dosage form of claim 8, wherein the progestogen particles are in micronized form.

10. The oral dosage form of claim 4, wherein the oral dosage form is a solid, monolithic dosage form.

11. The oral dosage form of claim 4, wherein the oral dosage form is a solid, monolithic dosage form comprising one or more polymers, wherein the progestogen compound is substantially dispersed in the one or more polymers.

12. The oral dosage form of claim 11, wherein at least one polymer is an enteric polymer.

13. The oral dosage form of claim 11, wherein at least one polymer is a hydrophilic polymer.

14. The oral dosage form of claim 11, wherein at least one polymer is a hydrophobic polymer.

15. A method of producing a contraception comprising administering to a subject an effective amount of a progestogen compound, the progestogen compound having the structure of formula (II):

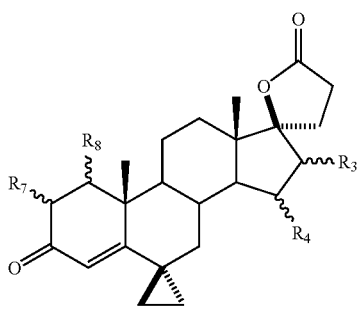

where:
R$_3$ and R$_4$ together form an α-CH$_2$ bridge between carbons 15 and 16 or a β-CH$_2$ bridge between carbons 15 and 16; and
R$_7$ and R$_8$ together form an α-CH$_2$ bridge between carbons 1 and 2.

16. The method of claim 15, wherein the progestogen compound has the structure of formula (IVc):

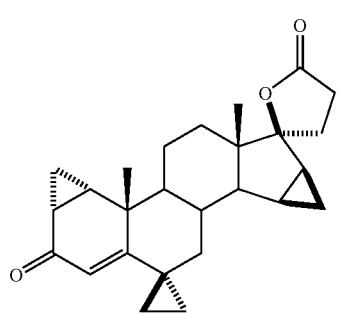

where R$_7$ and R$_8$ together form an α-CH$_2$ bridge between carbons 1 and 2.

17. The method of claim 15, further comprising administering an effective amount of an estrogen compound.

18. The method of claim 17, wherein the estrogen compound is ethinylestradiol.

19. The antimineralocorticoid compound of claim 1, wherein R$_1$ and R$_2$ are CH$_3$, the progestogen compound having the structure of formula (III):

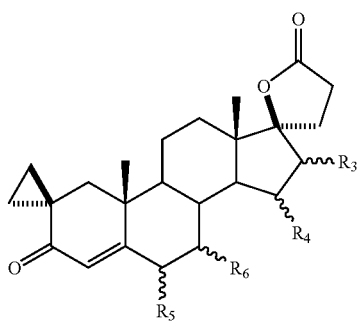

where R₃ and R₄ are hydrogens; or together form a α-CH₂ bridge between carbons 15 and 16; or a β-CH₂ bridge between carbons 15 and 16; and R₅ and R₆ together form a α-CH₂ bridge between carbons 6 and 7 or a β-CH₂ bridge between carbons 6 and 7.

20. The antimineralocorticoid compound of claim 1, wherein R₁ and R₂ are CH₃, R₃ and R₄ are H; and R₅ and R₆ are a β-CH₂ bridge, the progestogen compound having the structure of formula (IIIa):

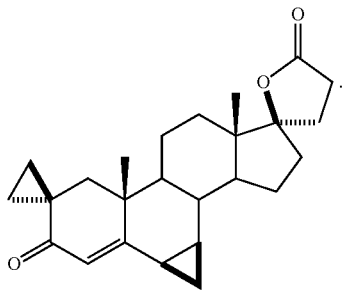

IIIa

21. The antimineralocorticoid compound of claim 1, wherein R₁ and R₂ are CH₃, R₃ and R₄ are H; and R₅ and R₆ are an α-CH₂ bridge, the progestogen compound having the structure of formula (IIIb):

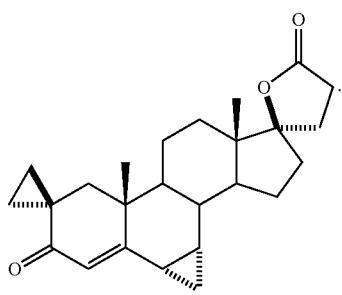

IIIb

22. The antimineralocorticoid compound of claim 1, wherein R₁ and R₂ are CH₃, R₃ and R₄ are an α-CH₂ bridge and R₅ and R₆ are an α-CH₂ bridge, the progestogen compound having the structure of formula (IIIc):

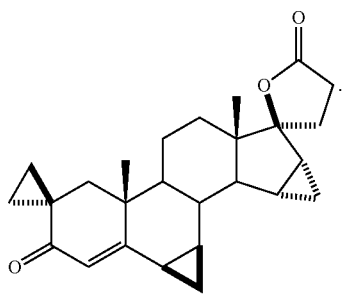

IIIc

23. The antimineralocorticoid compound of claim 1, wherein R₁ and R₂ are CH₃, R₃ and R₄ are an α-CH₂ bridge and R₅ and R₆ are an α-CH₂ bridge, the progestogen compound having the structure of formula (IIId):

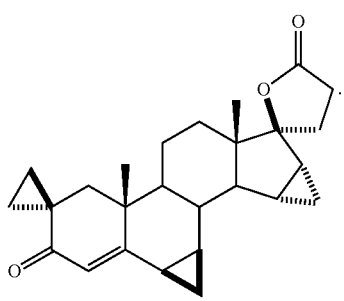

IIId

24. The antimineralocorticoid compound of claim 1, wherein R₁ and R₂ are CH₃, R₃ and R₄ are an β-CH₂ bridge and R₅ and R₆ are an β-CH₂ bridge, the progestogen compound having the structure of formula (IIIe):

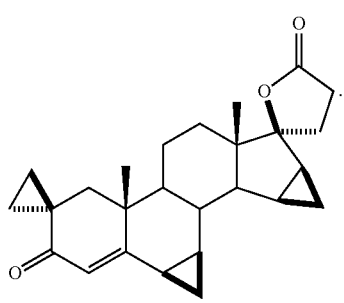

IIIe

25. The antimineralocorticoid compound of claim 1, wherein R₁ and R₂ are CH₃, R₃ and R₄ are an β-CH₂ bridge and R₅ and R₆ are an α-CH₂ bridge, the progestogen compound having the structure of formula (IIIf):

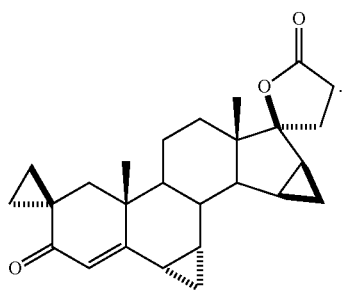

IIIf

* * * * *

UNITED STATES PATENT AND TRADEMARK OFFICE
CERTIFICATE OF CORRECTION

PATENT NO. : 7,960,368 B2  
APPLICATION NO. : 12/397996  
DATED : June 14, 2011  
INVENTOR(S) : Nickisch et al.

Page 1 of 1

It is certified that error appears in the above-identified patent and that said Letters Patent is hereby corrected as shown below:

Title Page:

Item (75) Inventors:

Please delete the city of inventor James W. Cessac "San Antonio, TX" and substitute therefor -- Floresville, TX --.

Item (73) Assignee:

Please delete "Everstra, Inc." and substitute therefor -- Evestra, Inc. --.

Signed and Sealed this  
Twentieth Day of September, 2011

David J. Kappos  
*Director of the United States Patent and Trademark Office*